US012636261B2

(12) United States Patent
Kwiecien

(10) Patent No.: US 12,636,261 B2
(45) Date of Patent: May 26, 2026

(54) TREATMENT OF INFLAMMATION INITIATED BY THE SPINAL CORD INJURY, THE TRAUMATIC BRAIN INJURY, STROKE, IN INHIBITION OF CEREBRAL AND SPINAL CORD EDEMA AND OF INFLAMMATION IN NEURODEGENERATIVE, IMMUNE MEDIATED AND INFECTIOUS DISEASES OF THE CENTRAL NERVOUS SYSTEM

(71) Applicant: Jacek M. Kwiecien, Hamilton (CA)

(72) Inventor: Jacek M. Kwiecien, Hamilton (CA)

( * ) Notice: Subject to any disclaimer, the term of this patent is extended or adjusted under 35 U.S.C. 154(b) by 565 days.

(21) Appl. No.: 17/346,726

(22) Filed: Jun. 14, 2021

(65) Prior Publication Data

US 2022/0395474 A1     Dec. 15, 2022

(51) Int. Cl.
    *A61K 31/12*        (2006.01)
    *A61P 25/28*        (2006.01)
(52) U.S. Cl.
    CPC .............. *A61K 31/12* (2013.01); *A61P 25/28* (2018.01)
(58) Field of Classification Search
    None
    See application file for complete search history.

(56) References Cited

U.S. PATENT DOCUMENTS

2020/0165608 A1*    5/2020   Ren ........................ A61K 38/47

OTHER PUBLICATIONS

Sleha et al., Strong Antimicrobial Effects of Xanthohumol and Beta-Acids from Hops against Clostridioides difficile Infection In Vivo. Antibiotics, 2021, 10, p. 1-11.*
Victor et al., Pharmacological activation of Nrf2 promotes wound healing. European Journal of Pharmacology, 2020, 886, p. 1-11.*
Yen et al., Neuroprotective Effects of Xanthohumol, a Prenylated Flavonoid from Hops (*Humulus lupulus*), in Ischemic Stroke of Rats. Journal of Agricultural and Food Chemistry, 2012, 60, p. 1937-1944.*
Henneman et al., Xanthohumol Protects Morphology and Function in a Mouse Model of Retinal Degeneration. Biochemistry and Molecular Biology, 2018, 59, 45-53.*
Zamzow et al., Xanthohumol improved cognitive flexibility in young mice. Brain Behavioral Research, 2014, 275, 1-10.*
Arnold SA, Hagg T. Anti-inflammatory treatments during the chronic phase of spinal cord injury improve locomotor function in adult mice. J Neurotrauma. 2011; 28: 1995-2002. doi: 10.1089/neu.2011. 1888.
Avula B, Ganzera M, Warnick JE, Feltenstein MW, Sufka KJ, Khan IA. High performance liquid chromatographic determination of xanthohumol in rat plasma, urine, and fecal samples. J Chromatogr Sci. 2004; 42: 378-382.
Chen X, Li Z, Hong H, Wang N, Chen J, Lu S, Zhang H, Zhang X, Bei C. Xanthohumol suppresses inflammation in chondrocytes and ameliorates osteoarthritis in mice. Biomed Pharmacother. 2021; 137: 111238. doi: 10.1016/j.biopha.2021.111238.
Cho YC, Kim HJ, Kim YJ, Lee KY, Choi HJ, Lee IS, Kang BY. Differential anti-inflammatory pathway by xanthohumol in IFN-gamma and LPS-activated macrophages. Int Immunopharmacol. 2008; 8: 567-573. doi: 10.1016/j.intimp.2007.12.017.
Cho YC, You SK, Kim HJ, Cho CW, Lee IS, Kang BY. Xanthohumol inhibits IL-12 production and reduces chronic allergic contact dermatitis. Int Immunopharmacol. 2010; 10: 556-561. doi: 10.1016/j.intimp.2010.02.002.
Cho J-M, Yun S-M, Choi Y-H, Heo J, Kim N-J, Kim S-H, Kim E-H. Xanthohumol prevents dextran sulfate sodium-induced colitis via inhibition of IKKβ/NF-κB signaling in mice. Oncotarget. 2017; 9: 866-880. doi:10.18632/oncotarget.23183.
Costa R, Negrao R, Valente I, Castela A, Duarte D, Guardao L, Magalhaews PJ, Rodrigues JA, Guimaraes JT, Gomes P, Soares R. Xanthohumol modulates inflammation, oxidative stress, and angiogenesis in type 1 diabetic rat skin wound healing. J Nat Prod. 2013; 76: 2047-2053. doi: 10.1021/np4002898.
Doddapattar P, Radivic B, Patankar JV, Obrowsky S, Jandl K, Nusshold C, Kolb D, Vujic N, Doshi L, Chandak PG, Goeritzer M, Ahammer H, Hoefler G, Sattler W, Kratky D. Xanthohumol ameliorates atherosclerotic plaque formation, hypercholesterolemia, and hepatic steatosis in ApoE-deficient mice. Mol Nutr Food Res. 2013; 57: 1718-1728. doi: 10.1002/mnfr.201200794.
Dorn C, Kraus B, Motyl M, Weiss TS, Gehring M, Scholmerich J, Heilmann J, Hellerbrand C. Xanthohumol, a chalcon derived from hops, inhibits hepatic inflammation and fibrosis. Mol Nutr Food Res. 2010a; 54 Suppl2: S205-213. doi: 10.1002/mnfr.200900314.
Dorn C, Bataille F, Gaebele E, Heilmann J, Hellerbrand C. Xanthohumol feeding does not impair organ function and homoeostasis in mice. Food Chem Toxicol. 2010b; 48: 1890-1897. doi: 10.1016/j.fct.2010. 04.030.

(Continued)

*Primary Examiner* — Po-Chih Chen
(74) *Attorney, Agent, or Firm* — Gowling WLG (Canada) LLP

(57)     ABSTRACT

The present invention pertains to the anti-inflammatory therapeutic effect of xantohumol in spinal cord injury (SCI). The continuous administration of xanthohumol for 1-8 weeks to SCI rats resulted in improved results in 4 clinical tests used and in lowering and faster elimination of macrophages from the SCI lesion. Since the infiltration of the SCI lesion by numerous phagocytic macrophages indicates a severe destructive inflammation of extraordinary longevity, administration of xanthohumol is neuroprotective and resulted in a better and faster recovery of the locomotor function and the strength and sensory function in the hind limbs, in a shorter period of paralysis of the urinary bladder and in the recovery of the body weight lost due to the SCI surgery. Since the traumatic brain injury (TBI) involving the white matter, and stroke involving the white matter initiate the severe destructive inflammation as in the SCI, the administration of xanthohumol is expected to be anti-inflammatory and neuroprotective in both brain diseases. Since neurodegenerative diseases including Alzheimer's disease, frontotemporal dementia and Parkinson's disease, immune mediated neuroinflammation including multiple sclerosis and neuromyelitis optica and cerebrospinal infections have inflammatory pathogenesis involving microgliosis and infiltration by macrophages, the administration of xanthohumol is expected to result in therapeutic inhibition of progression of all above diseases as well as of related neurodegenerative, immune mediated and infectious diseases of the brain and of the spinal cord.

20 Claims, 7 Drawing Sheets

(56)         References Cited

OTHER PUBLICATIONS

Dorn C, Massinger S, Wuzik A, Heilmann J, Hellebrand C. Xanthohumol suppresses inflammatory response to warm ischemia-reperfusion induced liver injury. Exp Mol Pathol. 2013; 94: 10-16. doi: 10.1016/j.yexmp.2012.05.003.

Henneman NF, Foster SL, Chrenek MA, Sellers JT, Wright CB, Schmidt RH, Nickerson JM, Boatright JH. Xanthohumol Protects Morphology and Function in a Mouse Model of Retinal Degeneration. Invest Ophthalmol Vis Sci. 2018; 59: 45-53. doi: 10.1167/iovs.17-22132.

Husson R, Frank N, Knauft J, Ittrich C, Owen R, Becker H, Gerhauser C. A safety study of oral xanthohumol administration and its influence on fertility in Sprague Dawley rats. Mol Nutr Food Res. 2005; 49: 861-867.

Jiao Y, Cao Y, Lu X, Wang J, Saitgareeva A, Kong X, Song C, Li J, Tian K, Zhang S, Bai M, Li S, Zhang H, Wang L. Xanthohumol protects neuron from cerebral ischemia injury in experimental stroke. Mol Biol Rep. 2020;47(4):2417-2425. doi: 10.1007/s11033-019-05128-4.

Kempuraj D, Thangavel R, Kempuraj DD, Ahmed ME, Selvakumar GP, Raikwar SP, Zaheer SA, Iyer SS, Govindarajan R, Chandrasekaran PN, Zaheer A. Neuroinflammation Induces Neurodegeneration, J Neuro Neurosurg Spine. 2016; 1 (1).

Khayyal MT, El-Hazek RM, El-Sabbagh WA, Frank J, Behnam D, Abdel-Tawab M. Micellar solubilization enhances the anti-inflammatory effect of xanthohumol. Phytomedicine. 2020; 71: 153233. doi: 10.1016/j.phymed.2020.153233.

Khupse RS, Erhardt PW. Total synthesis of xanthohumol. J Nat Prod 2007; 70: 1507-1509. doi: 10.1021/np070158y.

Kirchinger M, Bieler L, Tevini J, Vogl M, Haschke-Becher E, Felder TK, Coulliard-Despres S, Riepl H, Urmann C. Development and characterization of the neuroregenerative xanthohumol C/Hydroxypropyl-β-cyclodextrin complex suitable for parenteral administration. Planta Med. 2019; 85: 1233-1241. doi: 10.1055/a-1013-1276.

Koo WWK, Lasekan JB. Rice protein-based infant formula: current status and future development. Minerva Pediatr 2007; 59: 35-41.

Kubo Y, Suzuki M, Kufdo A, Yoshida K, Suzuki T, Ogasawara K, Ogawa A, Kurose A, Sawai T. Thrombin inhibitor ameliorates secondary damage in rat brain injury: suppression of inflammatory cells and vimentin-positive astrocytes. J Neurotrauma. 2000; 17: 163-72. doi: 10.1089/neu.2000.17.163.

Kwiecien JM, Jarosz B, Machova-Urdzikova L, Rola R, Dabrowski W. Subdural infusion of dexamethasone inhibits leukomyelitis after acute spinal cord injury in a rat model. Folia Neuropathol. 2015; 53:41-51.

Kwiecien JM, Jarosz B, Oakden W, Klapec M, Stanisz GJ, Delaney KH, Kotlinska-Hasiec E, Janik R, Rola R, Dabrowski W. An in vivo model of anti-inflammatory activity of subdural dexamethasone following the spinal cord injury. Pol J Neurol Neurosurg. 2016; 50: 7-15. DOI: 10.1016/j.pjnns.2015.10.006.

Kwiecien JM, Dabrowski W, Marzec-Kotarska B, Kwiecien-Delaney CJ, Yaron JR, Zhang J, Schutz L, Lucas AR. Myxoma virus derived immune modulating proteins, M-T7 and Serp-1, reduce early inflammation after spinal cord injury in the rat model. Folia Neuropathol. 2019; 57 (1): 41-50. doi.org/10.5114/fn.2019.83830.

Kwiecien JM, Dabrowski W, Kwiecien-Delaney BJ, Kwiecien-Delaney CJ, Siwicka-Gieroba D, Yaron JR, Zhang L, Delaney KH, Lucas AR. Neuroprotective effect of subdural infusion of Serp-1 in spinal cord trauma. Biomedicines. 2020b; 8: 372. doi:10.3390/biomedicines8100372.

Kwiecien JM, Zhang L, Yaron JR, Schutz LN, Kwiecien-Delaney CJ, Enkidia A. Awo EA, Burgin M, Dabrowski W, Lucas AR. Local Serpin Treatment via Chitosan-Collagen Hyrdogel after Spinal Cord Injury Reduces Tissue Damage and Improves Neurologic Function. Journal of Clinical Medicine. 2020, 9, 1221; doi:10.3390/jcm9041221.

Kwiecien JM. The pathogenesis of neurotrauma indicates targets for neuroprotective therapies. Curr Neuropharmacol. 2021a. doi:10.2174/1570159X19666210125153308.

Kwiecien JM, Yaron JR, Zhang L, Delaney KH, Lucas AR. Neurologic and histologic tests used to measure neuroprotective effectiveness of serpins. Methods Mol Biol. 2021; 2225: 227-239. doi: 10.1007/978-1-0716-1012-1_13.

Kwiecien JM, Dabrowski W, Yaron RJ, Zhang L, Delaney KH, Lucas AR. The role of astrogliosis in formation of the syrinx in spinal cord injury. Curr Neuropharmacol. 2021; 19: 294-303. doi: 10.2174/1570159X18666200720225222.

Lee IS, Lim J, Gal J, Kang JC, Kim HJ, Kang BY, Choi HJ. Anti-inflammatory activity of xanthohumol involves heme oxygenase-1 induction via NRF2-ARE signaling in microglial BV2 cells. Neurochem Int. 2011; 58: 153-160. doi: 10.1016/j.neuint.2010.11.008.

Legette L, Ma L, Reed RL, Miranda CL, Christensen JM, Rodriguez-Proteau R, Stevens JF. Pharmacokinetics of xanthohumol and metabolites in rats after oral and intravenous administration. Mol Nutr Food Res. 2012; 56: 466-474. doi: 10.1002/mnfr.201100554.

Li F, Yao Y, Huang H, Hao H, Ying M. Xanthohumol attenuates cisplatin-induced nephrotoxicity through inhibiting NF-κb and activating Nrf2 signaling pathways. International Immunopharmacology 2018; 61: 277-282. doi: 10.1016/j.intimp.2018.05.017.

Lima-Fontes M, Costa R, Rodrigues I, Soares R. Xanthohumol Restores Hepatic Glucolipid Metabolism Balance in Type 1 Diabetic Wistar Rats. Journal of Agricultural and Food Chemistry 2017; 65: 7433-7439. doi: 10.1021/acs.jafc.7b02595.

Lupinnacci E, Meijerink J, Vincken JP, Gabriele B, Gruppen H, Witkamp RF. Xanthohumol from hop (Humulus lupulus L.) is an efficient inhibitor of monocyte chemoattractant protein-1 and tumor necrosis factor-alpha release in LPS stimulated RAW 264.7 mouse macrophages and U937 human monocytes. J Agric Food Chem. 2009; 57: 7274-7281. doi: 10.1021/jf901244k.

Lv H, Liu Q, Wen Z, Feng H, Deng X, Ci X. Xanthohumol ameliorates lipopolysaccharide (LPS)-induced acute lung injury via induction of AMPK/GSK3β-Nrf2 signal axis. Redox Biol. 2017; 12: 311-324. doi: 10.1016/j.redox.2017.03.001.

Mallon S, Kwiecien JM, Karis JP. Imaging of Neurotrauma in Acute and Chronic Settings. Curr Neuropharmacol 2021; 19: 1178-1190. doi: 10.2174/1570159X19666210517114823.

Miranda CL, Stevens JF, Ivanov V, McCall M, Frei B, Deinzer ML, Buhler DR. Antioxidant and prooxidant actions of prenylated and nonprenylated chalcones and flavanones in vitro. J Agric Food Chem. 2016; 48: 3876-3884.

Monteiro R, Calhau C, Oliveira E Silva A, Penheiro-Silva S, Guerreiro S, Gartner F, Azevedo I, Soares R. Xanthohumol inhibits inflammatory factor production and angiogenesis in breast cancer xenografts. J Cell Biochem. 2008; 104: 1699-1707. doi: 10.1002/jcb.21738.

Negrao R, Costa R, Duarte D, Taveira Gomes T, Mendanha M, Moura L, Vasques L, Azevedo I, Soares R. Angiogenesis and inflammation signaling are targets of beer polyphenols on vascular cells. J Cell Biochem. 2010; 111: 1270-1279. doi: 10.1002/jcb.22850.

Negrao R, Costa R, Duarte D, Gomes TT, Coelho P, Guimaraes JT, Guardao L, Azevedo I, Soares R. Xanthohumol-supplemented beer modulates angiogenesis and inflammation in a skin wound healing model. Involvement of local adipocytes. J Cell Biochem. 2012; 113: 100-109.

Nookandeh A, Frank N, Steiner F, Ellinger R, Schneider B, Gerhauser C, Becker H. Xanthohumol metabolites in faeces of rats. Phytochemistry 2004; 65: 561-570.

Nozawa H. Xanthohumol, the chalcone from beer hops (Humulus lupulus L.), is the ligand for farnesoid X receptor and ameliorates lipid and glucose metabolism in KK-A(y) mice. Biochem Biophys Res Commun. 2005; 336: 754-761.

Oberbauer E, Urmann C, Steffenhagen C, Bieler L, Brunner D, Furtner T, Humpel C, Baumer B, Bandtlow C, Coulliard-Despres S, Rivera FJ, Riepl H, Aigner L. Chroman-like Cyclic Prenylflavonoids Promote Neuronal Differentiation and Neurite Outgrowth and Are Neuroprotective. J Nutr Biochem. 2013; 24: 1953-1962. doi: 10.1016/j.jnutbio.2013.06.005.

(56)  References Cited

OTHER PUBLICATIONS

Rancan L, Paredes SD, Garcia I, Munoz P, Garcia C, Lopez de Hontanar G, de la Fuente M, Vara E, Tresguerres JAF. Protective effect of xanthohumol against age-related brain damage. J Nutr Biochem. 2017; 49: 133-140. doi: 10.1016/j.jnutbio.2017.07.011.

Stevens JF, Page JE. Xanthohumol and related prenylflavonoids from hops and beer: to your good health! Phytochemistry 2004; 65: 1317-1330.

Vanhoecke BW, Delporte F, Van Braeckel E, Heyerick A, Depypere HT, Nuytinck M, De Keukeleire D, Bracke ME. A safety study of oral tangeretin and xanthohumol administration to laboratory mice. In Vivo. 2005; 19: 103-107.

Wang CC, Ho YH, Hung CF, Kuo JR, Wang SJ. Xanthohumol, an active constituent from hope, affords protection against kainic acid-induced excitotoxicity in rats. Neurochem Int. 2020; 133: 104629. doi: 10.1016/j.neuint.2019.104629.

Yamaguchi N, Satoh-Yamaguchi K, Ono M. In vitro evaluation of antibacterial, anticollagenase, and antioxidant activities of hop components (Humulus lupulus) addressing acne vulgaris. Phytomedicine. 2009; 16: 369-376. doi: 10.1016/j.phymed.2008.12.021.

Yang M, li N, Li F, Zhu Q, Liu X, Han Q, Wang Y, Chen Y, Zeng X, Lv Y, Zhang P, Yang C, Liu Z. Xanthohumol, a main prenylated chalcone from hops, reduces liver damage and modulates oxidative reaction and apoptosis in hepatitis C virus infected Tupaia belangeri. Int Immunopharmacol. 2013; 16: 466-474. doi: 10.1016/j.intimp. 2013.04.029.

Yen TL, Hsu CK, Lu WJ, Hsieh CY, Hsiao G, Chou DS, Wu GJ, Sheu JR. Neuroprotective effects of xanthohumol, a prenylated flavonoid from hops (Humulus lupulus), in ischemic stroke of rats. J Agric Food Chem. 2012; 60: 1937-1944. doi: 10.1021/jf204909p.

Zhang M, Zhang R, Zheng T, Chen Z, Ji G, Peng F, Wang W. Xanthohumol Attenuated Inflammation and ECM Degradation by Mediating HO-1/C/EBPβ Pathway in Osteoarthritis Chondrocytes. Front Pharmacol. 2021; 12: 680585. doi: 10.3389/fphar.2021. 680585.

* cited by examiner

Hind End Locomotor Test, SCI+1 Week

● no Tx
■ xanthohumol

SCI+2 Weeks

Effect of: treatment, p=0.0005

SCI+4 Weeks

Effect of: treatment, p<0.0001

SCI+6 Weeks

Effect of: treatment, p<0.0001

SCI+8 Weeks

Effect of: treatment, p=0.0018

Toe Pinch Withdrawal Test, SCI+1 Week

● no Tx
■ xanthohumol

SCI+2 Weeks

Effect of: treatment, p<0.0001

SCI+4 Weeks

Effect of: treatment, p<0.0001

SCI+6 Weeks

Effect of: treatment, p<0.0001

SCI+8 Weeks

Effect of: treatment, p=0.0049

Shorter duration of paralysis of urinary bladder the better.
For 4 weeks Tx group  the effect of treatment is significant, p=0.0386.
For 1, 2, 6, 8 weeks Tx group, the effect is not statistically significant.

Fig. 4.

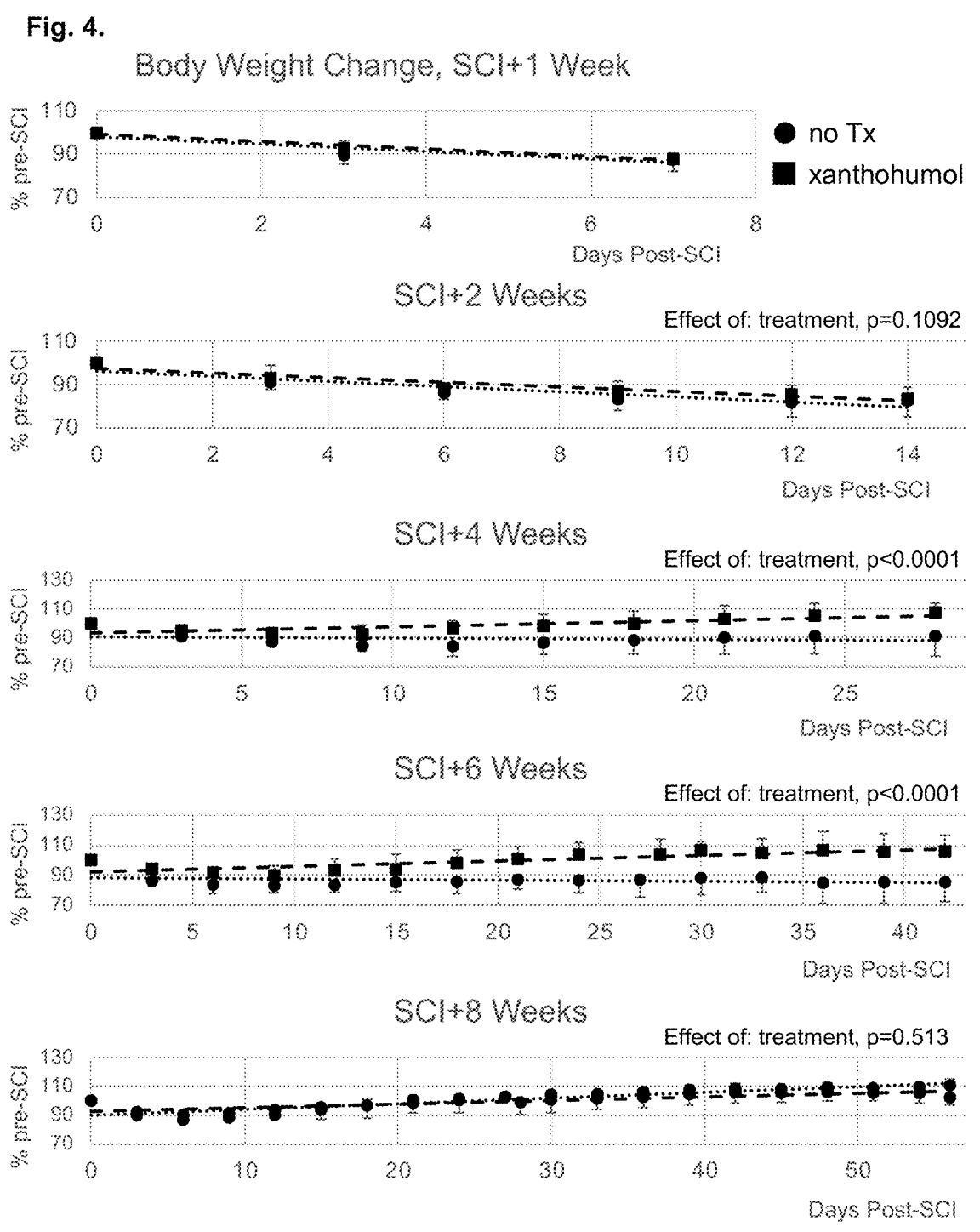

Body Weight Change, SCI+1 Week no Tx
xanthohumol

SCI+2 Weeks

Effect of: treatment, p=0.1092

SCI+4 Weeks

Effect of: treatment, p<0.0001

SCI+6 Weeks

Effect of: treatment, p<0.0001

SCI+8 Weeks

Effect of: treatment, p=0.513

| Treatment | Body Weight (g), average | Body weight (g), stdev | Average dose (mg/kg b.w.) |
|---|---|---|---|
| No Tx | 342.6 | 25.5 | 0 |
| 0.2 mg XN/day | 336.4 | 22.1 | 0.6 |
| 1.0 mg XN/day | 337.3 | 22.4 | 3.0 |
| 5.0 mg/XN day | 344.7 | 23.1 | 14.5 |

The effect treatment on macrophage counts in the cavity of injury (COI), the fewer macrophages the better.
Statistical significance for weeks of treatment:
1 week, p=0.0064; 2 weeks, p=0.0319; 4 weeks, p=0.0002; 6 weeks, p=0.0369; 8 weeks, p=0.3009.

TREATMENT OF INFLAMMATION INITIATED BY THE SPINAL CORD INJURY, THE TRAUMATIC BRAIN INJURY, STROKE, IN INHIBITION OF CEREBRAL AND SPINAL CORD EDEMA AND OF INFLAMMATION IN NEURODEGENERATIVE, IMMUNE MEDIATED AND INFECTIOUS DISEASES OF THE CENTRAL NERVOUS SYSTEM

CROSS-REFERENCE TO RELATED APPLICATIONS

List of Published US Patents.

| | | |
|---|---|---|
| 10,849,871 | Dec. 1, 2020 | Han et al |
| 10,829,441 | Nov. 10, 2020 | Nash et al |
| 10,537,566 | Jan. 21, | 2020 Smith |
| 10,369,222 | Aug. 6, 2019 | Han et al |
| 10,272,063 | Apr. 30, 2019 | Wu et al |
| 10,143,672 | Dec. 4, 2018 | Han et al |
| 10,071,106 | Sep. 11, 2018 | Marco Contelles et al |
| 10,060,933 | Aug. 28, 2018 | Julien et al |
| 9,988,340 | Jun. 5, 2018 | Kandula |
| 9,932,294 | Apr. 3, 2018 | Kandula |
| 9,867,816 | Jan. 16, 2018 | Weinstein |
| 9,827,220 | Nov. 28, 2017 | Wu et al |
| 9,782,362 | Oct. 10, 2017 | Back et al |
| 9,662,322 | May 30, 2017 | Knappertz |
| 9,617,213 | Apr. 11, 2017 | Rosello et al |
| 9,561,261 | Feb. 7, 2017 | Garvin et al |
| 9,539,249 | Jan. 10, 2017 | Weinstein |
| 9,556,097 | Jan. 31, 2017 | Gagos |
| 9,314,452 | Apr. 19, 2016 | Kalafer et al |
| 9,175,058 | Nov. 3, 2015 | Brod |
| 9,150,519 | Oct. 6, 2015 | Bombrun et al |
| 9,132,138 | Sep. 15, 2015 | Mak et al |
| 9,102,649 | Aug. 11, 2015 | Kandula |
| 9,101,580 | Aug. 11.2015 | Bennett et al |
| 9,068,002 | Jun. 30, 2015 | Prinz et al, |
| 9,061,020 | Jun. 23, 2015 | Weinstein |
| 9,050,305 | Jun. 9, 2015 | Wu et al |
| 8,906,357 | Dec. 9, 2014 | Moussy et al |
| 8,889,627 | Nov. 18, 2014 | Hallak et al |
| 8,697,060 | Apr. 15, 2014 | Bykovskaia et al |
| 8,491,913 | Jul. 23, 2013 | Offner et al |
| 8,454,965 | Jun. 4, 2013 | Martin et al, |
| 8,293,800 | Oct. 23, 2012 | Meier et al, |
| 7,968,293 | Jun. 28, 2011 | Reipert et al |
| 7,931,900 | Apr. 21, 2011 | Christie et al |
| 7,560,433 | Jul. 14, 2009 | Khan et al |
| 7,462,349 | Dec. 9, 2008 | Kalderon |
| 7,402,303 | Jul. 22, 2008 | Proudfoot et al |
| 7,368,421 | May 6, 2008 | Demoth et al |
| 7,258,859 | Aug. 21, 2007 | Martin et al |
| 7,255,887 | Aug. 14, 2007 | Rostami et al |
| 6,821,985 | Nov. 23.2004 | Chenard et al |
| 6,767,564 | Jul. 27, 2004 | Rostami et al |
| 6,667,317 | Dec. 23.2004 | Chenard et al |
| 6,649,617 | Adams | Nov. 18, 2003 |
| 6,323,188 | Weissman | Nov. 27, 2001 |
| 6,255,280 | Jul. 3, 2001 | Scheff |
| 6,174,875 | DeFranco et al | Jan. 16, 2001 |
| 5,817,684 | Fleisch et al | Oct. 6, 1999 |
| 5,206,226 | Apr. 27, 1993 | Sabin |
| 4,554,271 | Braughler et al | Nov. 19,1985 |

List of Published References.

Arnold S A, Hagg T. Anti-inflammatory treatments during the chronic phase of spinal cord injury improve locomotor function in adult mice. J Neurotrauma 2011; 28:1995-2002. doi: 10.1089/neu.2011.1888.

Avula B, Ganzera M, Warnick J E, Feltenstein M W, Sufka K J, Khan I A. High performance liquid chromatographic determination of xanthohumol in rat plasma, urine, and fecal samples. J Chromatogr Sci 2004; 42:378-382.

Batchelor P E, Tan S, Wills T E, Porritt M J, Howells D W. Comparison of inflammation in the brain and spinal cord following mechanical injury. J Neurotrauma 2008; 25:1217-25. doi: 10.1089/neu.2007.0308.

Blight A R. Macrophages and inflammatory damage in spinal cord injury. J Neurotrauma 1992; 9 Suppl 1: S83-91.

Bradley R, Langley B O, Ryan J J, Phipps J, Hanes D A, Stack E, Jansson J K, Metz T O, Stevens J F. Xanthohumol microbiome and signature in healthy adults (the XMaS trial): a phase I triple-masked, placebo-controlled clinical trial. Trials 2020; 21:835. doi: 10.1186/s13063-020-04769-2.

Cai W, Dai X, Chen J, Zhao J, Xu M, Zhang L, Yang B, Zhang W, Rocha M, Nakao T, Kofler J, Shi Y, Stetler R A, Hu X, Chen J. STAT6/Arg1 promotes microglia/macrophage efferocytosis and inflammation resolution in stroke mice. JCI Insight 2019; 4: e131355. doi: 10.1172/jci.insight.131355.

Chaban V, Clarke G J B, Skandsen T, Islam R, Einarsen C E, Vik A, Damas J K, Mollnes T E, Haberg A K, Pischke S E. Systemic Inflammation Persists the First Year after Mild Traumatic Brain Injury: Results from the Prospective Trondheim Mild Traumatic Brain Injury Study. J Neurotrauma 2020; 37:2120-2130. doi: 10.1089/neu.2019.6963.

Chen X, Li Z, Hong H, Wang N, Chen J, Lu S, Zhang H, Zhang X, Bei C. Xanthohumol suppresses inflammation in chondrocytes and ameliorates osteoarthritis in mice. Biomed Pharmacother. 2021; 137:111238. doi: 10.1016/j.biopha.2021.111238.

Chiu I M, Morimoto E T A, Goodarzi H, Liao J T, O'Keefe S, Phatnani H P, Muratet M, Carroll M C, Levy S, Tavazoi S, Myers R M, Maniatis T. A neurodegenerationspecific gene-expression signature of acutely isolated microglia from an amyotrophic lateral sclerosis mouse model. Cell Rep 2013; 4:385-401. doi: 10.1016/j.celrep.2013.06.018.

Cho Y C, Kim H J, Kim Y J, Lee K Y, Choi H J, Lee I S, Kang B Y. Differential anti-inflammatory pathway by xanthohumol in IFN-gamma and LPS-activated macrophages. Int Immunopharmacol 2008; 8:567-573. doi: 10.1016/j.intimp.2007.12.017.

Cho Y C, You S K, Kim H J, Cho C W, Lee I S, Kang B Y. Xanthohumol inhibits IL-12 production and reduces chronic allergic contact dermatitis. Int Immunopharmacol 2010; 10:556-561. doi: 10.1016/j.intimp.2010.02.002.

Cho J-M, Yun S-M, Choi Y-H, Heo J, Kim N-J, Kim S-H, Kim E-H. Xanthohumol prevents dextran sulfate sodium-induced colitis via inhibition of IKKβ/NF-κB signaling in mice. Oncotarget. 2017; 9:866-880. doi: 10.18632/oncotarget.23183.

Clausen F, Marklund N, Hillered L. Acute Inflammatory Biomarker Responses to Diffuse Traumatic Brain Injury in the Rat Monitored by a Novel Microdialysis Technique. J Neurotrauma 2019; 36:201-211. doi: 10.1089/neu.2018.5636.

Costa R, Negrao R, Valente I, Castela A, Duarte D, Guardao L, Magalhaews P J, Rodrigues J A, Guimaraes J T, Gomes P, Soares R. Xanthohumol modulates inflammation, oxidative stress, and angiogenesis in type 1 diabetic rat skin wound healing. J Nat Prod. 2013; 76:2047-2053. doi: 10.1021/np4002898.

Doddapattar P, Radivic B, Patankar J V, Obrowsky S, Jandl K, Nusshold C, Kolb D, Vujic N, Doshi L, Chandak P G, Goeritzer M, Ahammer H, Hoefler G, Sattler W, Kratky D. Xanthohumol ameliorates atherosclerotic plaque formation, hypercholesterolemia, and hepatic steatosis in ApoE-deficient mice. Mol Nutr Food Res 2013; 57:1718-1728. doi: 10.1002/mnfr.201200794.

Dorn C, Kraus B, Motyl M, Weiss T S, Gehring M, Scholmerich J, Heilmann J, Hellerbrand C. Xanthohumol, a chalcon.derived from hops, inhibits hepatic inflammation and fibrosis. Mol Nutr Food Res 2010a; 54 Suppl2: S205-213. doi: 10.1002/mnfr.200900314.

Dorn C, Bataille F, Gaebele E, Heilmann J, Hellerbrand C. Xanthohumol feeding does not impair organ function and homoeostasis in mice. Food Chem Toxicol 2010b; 48:1890-1897. doi: 10.1016/j.fct.2010.04.030.

Dorn C, Massinger S, Wuzik A, Heilmann J, Hellebrand C. Xanthohumol suppresses inflammatory response to warm ischemia-reperfusion induced liver injury. Exp Mol Pathol 2013; 94:10-16. doi: 10.1016/j: yexmp.2012.05.003.

Eldahshan W, Fagan S C, Ergul A. Within the neurovascular unit: Focus on microglia for stroke injury and recovery. Pharmacol Res Inflammation 2019; 147:104349. doi: 10.1016/j.phrs.2019.104349.

Elliott M B, Tuma R F, Amenta P S, Barbe M F, Jallo J I. Acute effects of a selective cannabinoid-2 receptor agonist on neuroinflammation in a model of traumatic brain injury. J Neurotrauma 2011; 28:973-81. doi: 10.1089/neu.2010.1672.

Esposito E, Ahn B J, Shi J, Nakamura Y, Park J H, Mandeville E T, Yu Z, Chan S J, Desai R, Hayakawa A, Ji X, Lo E H, Hayakawa K. Brain-to-cervical lymph node signaling after stroke. Nat Commun 2019; 10:5306. doi: 10.1038/s41467-019-13324-w.

Frugier T. Morganti-Kossmann M C, O'Reilly D, McLead C A. In situ detection of inflammatory mediators in post mortem human brain tissue after traumatic injury. J Neurotrauma 2010; 27:497-507. doi: 10.1089/neu.2009.1120.

Gensel J C, Zhang B. Macrophage activation and its role in repair and pathology after spinal cord injury. Brain Res. 2015; 1619:1-11. doi: 10.1016/j.brainres.2014.12.045.

Giulian D, Robertson C. Inhibition of mononuclear phagocytes reduces ischemic injury in the spinal cord. Ann Neurol 1990; 227:33-42. DOI: 10.1002/ana.410270107

Glushakova O Y, Johnson D, Hayes R L. Delayed increases in microvascular pathology after experimental traumatic brain injury are associated with prolonged inflammation, blood-brain barrier disruption, and progressive white matter damage. J Neurotrauma 2014; 31:1180-93. doi: 10.1089/neu.2013.3080.

Glushakova O Y, Glushakov A O, Borlongan C V, Valadka A B, Hayes R L, Glushakov A V. Role of Caspase-3-Mediated Apoptosis in Chronic Caspase-3-Cleaved Tau Accumulation and Blood-Brain Barrier Damage in the Corpus Callosum after Traumatic Brain Injury in Rats. J Neurotrauma 2018; 35:157-173. doi: 10.1089/neu.2017.4999.

Goldsmith Y, Kanner S, Zacs M, Frisca F, Pinto A R, Currie P D, Pinkas-Kramarski R. Rapamycin increases neuronal survival, reduces inflammation and astrocyte proliferation after spinal cord injury. Mol Cell Neurosci. 2015; 68:82-91. doi: 10.1016/j.mcn.2015.04.006.

Hazelton I, Yates A, Dale A, Roodselaar J, Akbar N, Ruitenberg M J, Anthony D C, Couch Y. Exacerbation of Acute Traumatic Brain Injury by Circulating Extracellular Vesicles. J Neurotrauma 2018; 35:639-651. doi: 10.1089/neu.2017.5049.

Henneman N F, Foster S L, Chrenek M A, Sellers J T, Wright C B, Schmidt R H, Nickerson J M, Boatright J H. Xanthohumol Protects Morphology and Function in a Mouse Model of Retinal Degeneration. Invest Ophthalmol Vis Sci 2018; 59:45-53. doi: 10.1167/iovs.17-22132.

Hsieh C L, Niemi E C, Wang S H, Lee C C, Bingham D, Zhang J, Cozen M L, Charo I, Huang E J, Liu J, Nakamura M C. CCR2 deficiency impairs macrophage infiltration and improves cognitive function after traumatic brain injury. J Neurotrauma 2014; 31:1677-88. doi: 10.1089/neu.2013.3252.

Huang W, Bhavsar A, Ward R E, Hall J C E, Priestley J V, Michael-Titus A T. Arachidonyl trifluoromethyl ketone is neuroprotective after spinal cord injury. J Neurotrauma 2009; 26:1429-34. doi: 10.1089/neu.2008.0835.

Husson R, Frank N, Knauft J, Ittrich C, Owen R, Becker H, Gerhauser C. A safety study of oral xanthohumol administration and its influence on fertility in Sprague Dawley rats. Mol Nutr Food Res 2005; 49:861-867.

Jayaraj R L, Azimullah S, Beiram R, Jalal F Y, Rosenberg G A. Neuroinflammation: friend and foe for ischemic stroke. J Neuroinflammation 2019; 16:142. doi: 10.1186/s12974-019-1516-2.

Jenkins D R, Craner M J, Esirti M M, DeLuca G C. Contribution of Fibrinogen to Inflammation and Neuronal Density in Human Traumatic Brain Injury. J Neurotrauma 2018; 35:2259-2271. doi: 10.1089/neu.2017.5291.

Jian Z, Liu R, Zhu X, Smerin D, Zhong Y, Gu L, Fang W, Xiong X. The Involvement and Therapy Target of Immune Cells After Ischemic Stroke Front Immunol 2019; 10:2167. doi: 10.3389/fimmu.2019.02167.

Jiao Y, Cao Y, Lu X, Wang J, Saitgareeva A, Kong X, Song C, Li J, Tian K, Zhang S, Bai M, Li S, Zhang H, Wang L. Xanthohumol protects neuron from cerebral ischemia injury in experimental stroke. Mol Biol Rep 2020; 47 (4): 2417-2425. doi: 10.1007/s11033-019-05128-4.

Jin R, Yang G, Li G. Inflammatory mechanisms in ischemic stroke: role of inflammatory cells. J Leukoc Biol 2010; 87:779-89. doi: 10.1189/jlb.1109766.

Kanazawa M, Ninomyya I, Hatakeyama M, Takahashi T, Shimohata T. Microglia and Monocytes/Macrophages Polarization Reveal Novel Therapeutic Mechanism against Stroke. Int J Mol Sci 2017; 18:2135. doi: 10.3390/ijms18102135.

Kempuraj D, Thangavel R, Natteru P A, Selvakumar G P, Saeed D, Zahoor H, Zaheer S, Iyer S S, Zaheer A. Neuroinflammation Induces Neurodegeneration. J Neurol Neurosurg Spine 2016; 1:1003.

Kempuraj D, Thangavel R, Kempuraj D D, Ahmed M E, Selvakumar G P, Raikwar S P, Zaheer S A, Iyer S S, Govindarajan R, Chandrasekaran P N, Zaheer A. Neuroprotective effects of flavone luteolin in neuroinflammation and neurotrauma. Biofactors 2021; 47:190-197. DOI: 10.1002/biof 0.1687

Khayyal M T, El-Hazek R M, El-Sabbagh W A, Frank J, Behnam D, Abdel-Tawab M. Micellar solubilization enhances the anti-inflammatory effect of xanthohumol. Phytomedicine 2020; 71:153233. doi: 10.1016/j.phymed.2020.153233.

Khupse R S, Erhardt P W. Total synthesis of xanthohumol. J Nat Prod 2007; 70:1507-1509. doi: 10.1021/np070158y.

Kim C C, Nakamura C C, Hsieh C L. Brain trauma elicits non-canonical macrophage activation states. J Neuroinflammation 2016; 13:117. doi: 10.1186/s12974-016-0581-z.

Kirchinger M, Bieler L, Tevini J, Vogl M, Haschke-Becher E, Felder T K, Coulliard-Despres S, Riepl H, Urmann C. Development and characterization of the neuroregenerative xanthohumol C/Hydroxypropyl-β-cyclodextrin complex suitable for parenteral administration. Planta Med 2019; 85:1233-1241. doi: 10.1055/a-1013-1276.

Kubo Y, Suzuki M, Kufdo A, Yoshida K, Suzuki T, Ogasawara K, Ogawa A, Kurose A, Sawai T. Thrombin inhibitor ameliorates secondary damage in rat brain injury: suppression of inflammatory cells and vimentin-positive astrocytes. J Neurotrauma 2000; 17:163-72. doi: 10.1089/neu.2000.17.163

Kwiecien J M. Cellular mechanisms of white matter regeneration in adult dysmyelinated rat model. Folia Neuropathol 2013, 51:189-202. doi: 10.5114/fn.2013.37703.

Kwiecien J M, Jarosz B, Machova-Urdzikova L, Rola R, Dabrowski W. Subdural infusion of dexamethasone inhibits leukomyelitis after acute spinal cord injury in a rat model. Folia Neuropathol 2015; 53:41-51.

Kwiecien J M, Jarosz B, Oakden W, Klapec M, Stanisz G J, Delaney K H, Kotlinska-Hasiec E, Janik R, Rola R, Dabrowski W. An in vivo model of anti-inflammatory activity of subdural dexamethasone following the spinal cord injury. Pol J Neurol Neurosurg 2016; 50:7-15. DOI: 10.1016/j.pjnns.2015.10.006.

Kwiecien J M, Dabrowski W, Marzec-Kotarska B, Kwiecien-Delaney C J, Yaron J R, Zhang J, Schutz L, Lucas A R. Myxoma virus derived immune modulating proteins, M-T7 and Serp-1, reduce early inflammation after spinal cord injury in the rat model. Folia Neuropathol 2019; 57 (1): 41-50. doi.org/10.5114/fn.2019.83830

Kwiecien J M, Dabrowski W, Dąbrowska-Bouta B, Sulkowski G, Oakden W, Kwiecien-Delaney C J, Yaron J R, Zhang L, Marzec-Kotarska B, Stanisz G J, Karis J P, Struzynska L, Lucas A R. Protracted inflammation extends damage after spinal cord injury. PLOS ONE 2020a; 15 (3): e0226584. https://doi.org/10.1371/journal.pone.0226584.

Kwiecien J M, Dabrowski W, Kwiecien-Delaney B J, Kwiecien-Delaney C J, Siwicka-Gieroba D, Yaron J R, Zhang L, Delaney K H, Lucas A R. Neuroprotective effect of subdural infusion of Serp-1 in spinal cord trauma. Biomedicines 2020b; 8:372. doi: 10.3390/biomedicines8100372.

Kwiecien J M, Zhang L, Yaron J R, Schutz L N, Kwiecien-Delaney C J, Enkidia A. Awo E A, Burgin M, Dabrowski W, Lucas A R. Local chitosan-serpin injection after spinal cord injury reduces inflammatory damage and improves neurologic function. J Clin Med 2020c April 23; 9 (4). pii: E1221. doi: 10.3390/jcm9041221.

Kwiecien J M. The pathogenesis of neurotrauma indicates targets for neuroprotective therapies. Curr Neuropharmacol 2021a. doi: 10.2174/1570159X19666210125153308.

Kwiecien J M. Barriers to axonal regeneration after spinal cord injury, a current perspective. Neuroregen Res 2021b; 17:85-86.

Kwiecien J M, Yaron J R, Zhang L, Delaney K H, Lucas A R. Neurologic and histologic tests used to measure neuroprotective effectiveness of serpins. Methods Mol Biol 2021; 2225:227-239. doi: 10.1007/978-1-0716-1012-1_13.

Kwiecien J M, Dabrowski W, Yaron R J, Zhang L, Delaney K H, Lucas A R. The role of astrogliosis in formation of the syrinx in spinal cord injury. Curr Neuropharmacol 2021; 19:294-303. doi: 10.2174/1570159X18666200720225222.

Kwiecien J M. "The Pathogenesis of Neurotrauma with Introduction to Neuroprotective and Neuroregenerative Treatments". Nova Science Publishers, Hauppauge N Y, USA. 2022.

Lambertsen K L, Biber K, Finsen B. Inflammatory cytokines in experimental and human stroke. J Cereb Blood Flow Metab 2012; 32:1677-98. doi: 10.1038/jcbfm.2012.88.

Lee I S, Lim J, Gal J, Kang J C, Kim H J, Kang B Y, Choi H J. Anti-inflammatory activity of xanthohumol involves heme oxygenase-1 induction via NRF2-ARE signaling in microglial BV2 cells. Neurochem Int 2011; 58:153-160. doi: 10.1016/j.neuint.2010.11.008.

Lee J Y, Kang S R, Yune T Y. Fluoxetine prevents oligodendrocyte cell death by inhibiting microglia activation after spinal cord injury. J Neurotrauma 2015; 32:633-44. doi: 10.1089/neu.2014.3527.

Lee J Y, Choi H Y, Park C S, Ju B G, Yune T Y. Mithramycin A Improves Functional Recovery by Inhibiting BSCB Disruption and Hemorrhage after Spinal Cord Injury. J Neurotrauma 2018; 35:508-520. doi: 10.1089/neu.2017.5235.

Legette L, Ma L, Reed R L, Miranda C L, Christensen J M, Rodriguez-Proteau R, Stevens J F. Pharmacokinetics of xanthohumol and metabolites in rats after oral and intravenous administration. Mol Nutr Food Res 2012; 56:466-474. doi: 10.1002/mnfr.201100554.

Li F, Yao Y, Huang H, Hao H, Ying M. Xanthohumol attenuates cisplatin-induced nephrotoxicity through inhibiting NF-κB and activating Nrf2 signaling pathways. 2018; 61:277-282. doi: 10.1016/j.intimp.2018.05.017.

Li M, Rong Z-J, Cao Y, Jiang L-Y, Zhong D, Li C-J, Sheng X-L, Hu J-Z, Lu H-B. Utx Regulates the NF-κB Signaling Pathway of Natural Stem Cells to Modulate Macrophage Migration during Spinal Cord Injury. J Neurotrauma 2021; 38:353-364. doi: 10.1089/neu.2020.7075.

Lima-Fontes M, Costa R, Rodrigues I, Soares R. Xanthohumol Restores Hepatic Glucolipid Metabolism Balance in Type 1 Diabetic Wistar Rats. 2017; 65:7433-7439. doi: 10.1021/acs.jafc.7b02595.

Liu G, Fiala M, Mizwicki M T, Sayre J, Magpantay L, Siani A, Mahanian M, Chattopadhyay M, La Cava A, Wiedau-Pazos M. Neuronal phagocytosis by inflammatory macrophages in ALS spinal cord: inhibition of inflammation by resolvin D1. Am J Neurodegener Dis 2012; 1:60-74.

Luchetti S, Beck K D, Galvan M D, Silva R, Cummings B J, Anderson A J. Comparison of immunopathology and locomotor recovery in C57B L/6, BUB/BnJ, and NOD-SCID mice after contusion spinal cord injury. J Neurotrauma 2010; 27:411-21. doi: 10.1089/neu.2009.0930.

Lupinnacci E, Meijerink J, Vincken J P, Gabriele B, Gruppen H, Witkamp R F. Xanthohumol from hop (Humulus lupulus L.) is an efficient inhibitor of monocyte chemoattractant protein-1 and tumor necrosis factor-alpha release in LPS stimulated RAW 264.7 mouse macrophages and U937 human monocytes. J Agric Food Chem 2009; 57:7274-7281. doi: 10.1021/jf901244k.

Lv H, Liu Q, Wen Z, Feng H, Deng X, Ci X. Xanthohumol ameliorates lipopolysaccharide (LPS)-induced acute lung injury via induction of AMPK/GSK3ß-Nrf2 signal axis. Redox Biol 2017; 12:311-324. doi: 10.1016/j.redox.2017.03.001.

Mallon S, Kwiecien J M, Karis J P. Imaging of Neurotrauma in Acute and Chronic Settings. Curr Neuropharmacol 2021 May 16. doi: 10.2174/1570159X19666210517114823.

Mietto B S, Mostacada K, Blanco Martinez A M. Neurotrauma and inflammation: CNS and PNS responses. Mediators Inflamm. 2015; 2015:251204. doi: 10.1155/2015/251204.

Miranda C L, Stevens J F, Ivanov V, McCall M, Frei B, Deinzer M L, Buhler D R. Antioxidant and prooxidant actions of prenylated and nonprenylated chalcones and flavanones in vitro. J Agric Food Chem 2016; 48:3876-3884.

Monteiro R, Calhau C, Oliveira E Silva A, Penheiro-Silva S, Guerreiro S, Gartner F, Azevedo 1, Soares R. Xanthohumol inhibits inflammatory factor production and angiogenesis in breast cancer xenografts. J Cell Biochem 2008; 104:1699-1707. doi: 10.1002/jcb.21738.

Morganti J M, Riparip L-K, Chou A, Liu S, Gupta N, Rosi S. Age exacerbates the CCR2/5-mediated neuroinflammatory response to traumatic brain injury. J Neuroinflammation 2016a; 13:80. doi: 10.1186/s12974-016-0547-1.

Morganti J M, Riparip L-K, Rosi S. Call Off the Dog (ma): M1/M2 Polarization Is Concurrent following Traumatic Brain Injury. PLOS One 2016b; 11: e0148001. doi: 10.1371/journal.pone.0148001.

Nakajima H, Uchida K, Rodriguez Guerro A, Watanabe S, Sugita D, Takeura N, Yoshida A, Long G, Wright K T, Johnson W E B, Baba H. Transplantation of mesenchymal stem cells promotes an alternative pathway of macrophage activation and functional recovery after spinal cord injury. J Neurotrauma 2012; 29:1614-25. doi: 10.1089/neu.2011.2109.

Nakamura K, Shichita T. Cellular and molecular mechanisms of sterile inflammation in ischaemic stroke. J Biochem 2019; 165:459-464. doi: 10.1093/jb/mvz017.

Negrao R, Costa R, Duarte D, Taveira Gomes T, Mendanha M, Moura L, Vasques L, Azevedo I, Soares R. Angiogenesis and inflammation signaling are targets of beer polyphenols on vascular cells. J Cell Biochem 2010; 111: 1270-1279. doi: 10.1002/jcb.22850.

Negrao R, Costa R, Duarte D, Gomes T T, Coelho P, Guimaraes J T, Guardao L, Azevedo I, Soares R. Xanthohumol-supplemented beer modulates angiogenesis and inflammation in a skin wound healing model. Involvement of local adipocytes. J Cell Biochem 2012; 113:100-109.

Nookandeh A, Frank N, Steiner F, Ellinger R, Schneider B, Gerhauser C, Becker H. Xanthohumol metabolites in faeces of rats. Phytochemistry 2004; 65:561-570.

Norden D M, Faw T D, McKim D B, Deibert R J, Fisher L C, Sheridan J F, Godbout J P, Basso D M. J Neurotrauma Bone Marrow-Derived Monocytes Drive the Inflammatory Microenvironment in Local and Remote Regions after ThoracicSpinal Cord Injury. 2019; 36:937-949. doi: 10.1089/neu.2018.5806.

Nowak B, Pozniak B, Poplonski J, Bobak L, Matuszewska A, Kwiatkowska J, Dziewiszek W, Huszcza E, Szelag A. Pharmacokinetics of xanthohumol in rats of both sexes after oral and intravenous administration of pure xanthohumol and prenylflavonoid extract. Adv Clin Exp Med 2020; 29:1101-1109. Available at doi: 10.17219/acem/126293.

Nozawa H. Xanthohumol, the chalcone from beer hops (*Humulus lupulus* L.), is the ligand for farnesoid X receptor and ameliorates lipid and glucose metabolism in KK-A(y) mice. Biochem Biophys Res Commun 2005; 336:754-761.

Oberbauer E, Urmann C, Steffenhagen C, Bieler L, Brunner D, Furtner T, Humpel C, Baumer B, Bandtlow C, Coulliard-Despres S, Rivera F J, Riepl H, Aigner L. Chroman-like Cyclic Prenylflavonoids Promote Neuronal Differentiation and Neurite Outgrowth and Are Neuroprotective. J Nutr Biochem. 2013; 24:1953-1962. doi: 10.1016/j.jnutbio.2013.06.005.

Patterson Z R, Holahan M R. Understanding the neuroinflammatory response following concussion to develop treatment strategies. Front Cell Neurosci 2012; 6:58. doi: 10.3389/fncel.2012.00058.

Perez-Polo J R, Rea H C, Johnson K M, Parsley M A, Unabia G C, Xu G, Infante S K, Dewitt D S, Hulsebosch C E. Inflammatory consequences in a rodent model of mild traumatic brain injury. J Neurotrauma 2013; 30:727-40. doi: 10.1089/neu.2012.2650.

Popovich P G, Wei P, Stokes B T. Cellular inflammatory response after spinal cord injury in Sprague-Dawley and Lewis rats. J Comp Neurol 1997; 377:443-464. DOI: 10.1002/(sici) 1096-9861 (19970120) 377: 3<443::aid-cne10>3.0.co;2-s Rancan L, Paredes S D, Garcia I, Munoz P, Garcia C, Lopez de Hontanar G, de la Fuente M, Vara E, Tresguerres J A F. Protective effect of xanthohumol against age-related brain damage. J Nutr Biochem 2017; 49:133-140. doi: 10.1016/j.jnutbio.2017.07.011.

Saber M, Kokiko-Cochran O, Puntambekar S S, Lathia J D, Lamb B T. Triggering Receptor Expressed on Myeloid Cells 2 Deficiency Alters Acute Macrophage Distribution and Improves Recovery after Traumatic Brain Injury. J Neurotrauma 2017; 34:423-435. doi: 10.1089/neu.2016.4401.

Schroeter M, Jander S, Huitinga I, Witte O W, Stoll G. Phagocytic response in photochemically induced infarction of rat cerebral cortex. Stroke. 1977; 28:382-386. DOI: 10.1161/01.str.28.2.382

Schwab J M, Seid K, Schluesener H J. Traumatic brain injury induces prolonged accumulation of cyclooxygenase-1 expressing microglia/brain macrophages in rats. J Neurotrauma 2001; 18:881-90. doi: 10.1089/089771501750451802.

Shekar S, Cunningham M W, Pabbidi M R, Wang S, Booz G W, Fan F. Targeting vascular inflammation in ischemic stroke: Recent developments on novel immunomodulatory approaches. Eur J Pharmacol 2018; 833:531-544. doi: 10.1016/j.ejphar.2018.06.028.

Stevens J F, Page J E. Xanthohumol and related prenylflavonoids from hops and beer: to your good health! Phytochemistry 2004; 65:1317-1330.

Takamyia M, Fujita S, Saigusa K, Aoki Y. Simultaneous detections of 27 cytokines during cerebral wound healing by multiplexed bead-based immunoassay for wound age estimation. J Neurotrauma 2007; 24:1833-44. doi: 10.1089/neu.2007.0336.

Takigawa T, Yonezawa T, Yoshitaka T, Minaguchi J, Kurosaki M, Tanaka M, Sado Y, Ohtsuka A, Ozaki T, Ninomiya Y. Separation of the perivascular basement membrane provides a conduit for inflammatory cells in a mouse spinal cord injury model. J Neurotrauma 2010; 27:739-51. doi: 10.1089/neu.2009.1111.

Tatara Y, Shimada R, Kibayashi K. Effects of Preexisting Diabetes Mellitus on the Severity of Traumatic Brain Injury. J Neurotrauma 2021; 38:886-902. doi: 10.1089/neu.2020.7118.

Taylor A R, Welsh C J, Young C, Spoor E, Kerwin S C, Griffin J F, Levine G J, Cohen N D, Levine J M. Cerebrospinal fluid inflammatory cytokines and chemokines in naturally occurring canine spinal cord injury. J Neurotrauma 2014; 31:1561-9. doi: 10.1089/neu.2014.3405.

Truettner J S, Bramlett H M, Dietrich W D. Hyperthermia and Mild Traumatic Brain Injury: Effects on Inflammation and the Cerebral Vasculature. J Neurotrauma 2018; 35:940-952. doi: 10.1089/neu.2017.5303

Vanhoecke B W, Delporte F, Van Braeckel E, Heyerick A, Depypere H T, Nuytinck M, De Keukeleire D, Bracke M E. A safety study of oral tangeretin and xanthohumol administration to laboratory mice. In Vivo 2005; 19:103-107.

Wang Y, Huang Y, Xu Y, Ruan W, Wang H, Zhang Y, Saavedra J M, Zhang L, Huang Z, Pang T. A Dual AMPK/Nrf2 Activator Reduces Brain Inflammation After Stroke by Enhancing Microglia M2 Polarization. Antioxid Redox Signal 2018; 28:141-163. doi: 10.1089/ars.2017.7003.

Wang C C, Ho Y H, Hung C F, Kuo J R, Wang S J. Xanthohumol, an active constituent from hope, affords protection against kainic acid-induced excitotoxicity in rats. Neurochem Int 2020; 133:104629. doi: 10.1016/j.neuint.2019.104629.

Wicher G, Wallenquist U, Lei Y, Enoksson M, Li X, Fuchs B, Hamdeh S A, Marklund N, Hillered L, Nilsson G, Forsberg-Nilsson K. Interleukin-33 Promotes Recruitment of Microglia/Macrophages in Response to Traumatic Brain Injury. J Neurotrauma 2017; 34:3173-3182. doi: 10.1089/neu.2016.4900.

Witcher K G, Bray C E, Chunchai T, Zhao F, O'Neil S M, Gordillo A J, Campbell W A, McKim D B, Liu X, Dziabis J E, Quan N, Eiferman D S, Fischer A J, Kokiko-Cochran O N, Askwith C, Godbout J P. Traumatic Brain Injury Causes Chronic Cortical Inflammation and Neuronal Dysfunction Mediated by Microglia. J Neurosci. 2021; 41:1597-1616. doi: 10.1523/JNEUROSCI.2469-20.2020.

Wofford K L, Loane D J, Cullen D K. Acute drivers of neuroinflammation in traumatic brain injury. Neural Regen Res 2019; 14:1 481-1489. doi: 10.4103/1673-5374.255958

Yamaguchi N, Satoh-Yamaguchi K, Ono M. In vitro evaluation of antibacterial, anticollagenase, and antioxidant activities of hop components (*Humulus lupulus*) addressing acne vulgaris. Phytomedicine 2009; 16:369-376. doi: 10.1016/j.phymed.2008.12.021.

Yang M, li N, Li F, Zhu Q, Liu X, Han Q, Wang Y, Chen Y, Zeng X, Lv Y, Zhang P, Yang C, Liu Z. Xanthohumol, a main prenylated chalcone from hops, reduces liver damage and modulates oxidative reaction and apoptosis in hepatitis C virus infected Tupaia belangeri. Int Immunopharmacol 2013; 16:466-474. doi: 10.1016/j.intimp.2013.04.029.

Yen T L, Hsu C K, Lu W J, Hsieh C Y, Hsiao G, Chou D S, Wu G J, Sheu J R. Neuroprotective effects of xanthohumol, a prenylated flavonoid from hops (*Humulus lupulus*), in ischemic stroke of rats. J Agric Food Chem 2012; 60:1937-1944. doi: 10.1021/jf204909p.

Zanier E R, Marchesi F, Ortolano F, Perego C, Arabian M, Zoerle T, Sammali E, Pischiutta F, De Simoni M-G. Fractalkine Receptor Deficiency Is Associated with Early Protection but Late Worsening of Outcome following Brain Trauma in Mice. J Neurotrauma 2016; 33:1060-72. doi: 10.1089/neu.2015.4041.

Zhang D, Lu Z, Man J, Cui K, Fu X, Yu L, Gao Y, Liao L, Xiao Q, Gou R, Zhang Y, Zhang Z, Liu X, Lu H, Wang J. Wnt-3a alleviates neuroinflammation after ischemic stroke by modulating the responses of microglia/macrophages and astrocytes. Int Immunopharmacol 2019; 75:105760. doi: 10.1016/j.intimp.2019a.105760.

Zhang W, Zhao J, Wang R, Jiang M, Ye Q, Smith A D, Chen J, Shi Y. Macrophages reprogram after ischemic stroke and promote efferocytosis and inflammation resolution in the mouse brain. CNS Neurosci Ther 2019; 25:1329-1342. doi: 10.1111/cns.13256.

Zhang M, Zhang R, Zheng T, Chen Z, Ji G, Peng F, Wang W. Xanthohumol Attenuated Inflammation and ECM Degradation by Mediating HO-1/C/EBPβ Pathway in Osteoarthritis Chondrocytes. Front Pharmacol 2021; 12:680585. doi: 10.3389/fphar.2021.680585.

Zhao S-C, Ma L-S, Chu Z-H, Xu H, Wu W-Q, Liu F. Regulation of microglial activation in stroke. Acta Pharmacol Sin 2017; 38:445-458. doi: 10.1038/aps.2016.162.

Zheng Y, He R, Wang P, Shi Y, Zhao L, Liang J. Exosomes from LPS-stimulated macrophages induce neuroprotection and functional improvement after ischemic stroke by modulating microglial polarization. Biomater Sci 2019; 7:2037-2049. doi: 10.1039/c8bm01449c.

STATEMENT REGARDING FEDERALLY SPONSORED RESEARCH OR DEVELOPMENT (IF APPLICABLE)

Not applicable.

THE NAMES OF THE PARTIES TO A JOINT RESEARCH AGREEMENT

Not applicable.

REFERENCE TO SEQUENCE LISTING, A TABLE, OR A COMPUTER PROGRAM LISTING COMPACT DISC APPENDIX (IF APPLICABLE)

Not applicable.

STATEMENT REGARDING PRIOR DISCLOSURES BY THE INVENTOR OR A JOINT INVENTOR

Not applicable.

BACKGROUND OF THE INVENTION

Field of the Invention

The present invention is about a therapeutic method where oral administration of xanthohumol improves clinical and pathologic outcomes in the spinal cord injury (SCI), in the traumatic brain injury (TBI), in the resection neurosurgery and in stroke, and also in cerebral edema and in spinal cord edema.

Discussion of Background Information

Treatments for neurotrauma and vascular occlusive accidents resulting in stroke are lacking or are generally not effective. This unfortunate status has not been helped by poor understanding of the pathogenesis of these diseases with futile therapeutic strategies aimed at wrong pathologic targets. Neurotrauma in the spinal cord injury (SCI), in the traumatic brain injury (TBI) and in neurosurgical resection that results in a locally massive necrosis and hemorrhage in the white matter, initiate a severe and extraordinarily protracted inflammation fueled by potently immunogenic damaged myelin. Although stroke is not initiated by a traumatic event but rather by an occlusive vascular accident in the brain, the resulting ischemia, locally massive necrosis and sometimes hemorrhages involving the white matter, initiate the same severe inflammatory response. The pathogenesis of neurotrauma and stroke has recently been elucidated in a systematic study on the rat model of SCI [Kwiecien et al, 2020a; Kwiecien, 2022], where macrophage-rich infiltration is directed at removing myelin-rich necrotic debris and red blood cells and also results in elevation of pro-inflammatory cytokines including IL-1β, IL-6 and IFN-γ, and chemokines, and in damage to the spinal cord around the initial lesion. Since the human brain is rich in the white matter content and TBI, surgical resection and stroke often involve this myelin-rich tissue, the myelin-rich spinal cord is an appropriate model of the white matter injury in cerebral trauma and stroke. Rodent models of cerebral trauma and stroke involve primarily a gray matter injury since the white matter content in the brain of mice and rats is low. A gray matter injury initiates inflammation that is much less severe and self-limiting. Severe inflammation initiated by neurotrauma (SCI, TBI, neurosurgical resection) and stroke involving the white matter, is associated with damage to small and capillary blood vessels in the CNS around the inflammatory lesion leading to leaking of excess fluid that can overwhelm water management by astrocytic systems leading to cerebral edema or spinal cord edema [Kwiecien et al, 2021d, Mallon et al, 2021]. It is considered that neuroinflammation initiated by TBI and SCI can be more damaging to neurological outcome than neurotrauma itself [Patterson & Holahan, 2012; Wofford et al, 2019]. While stroke [Schroeter et al, 1977] or neurotrauma-initiated inflammation has been recognized in the animal models of SCI [Arnold & Hagg, 2011; Batchelor et al, 2008; Huang et al, 2009; Lee et al, 2015, 2018; Mietto et al, 2015; Taylor et al, 2014] and in TBI [Clausen et al, 2019; Elliot et al, 2011; Glushakova et al, 2014, 2018; Hazelton et al, 2018; Kempuraj et al, 2021; Morganti et al, 2016a, 2016b; Perez-Polo et al, 2013; Takamyia et al, 2007; Tatara et al, 2021; Treuttner et al, 2018; Witcher et al, 2021; Wofford et al, 2019; Zanier et al, 2016] and in human neurotrauma [Chaban et al, 2020; Frugier et al, 2010; Jenkins et al, 2018], with macrophages starting to infiltrate the site of injury by day 3 [Batchelor et al, 2008; Blight 1992; Gensel et al, 2015; Giulian & Robertson, 1990; Goldsmith et al, 2015; Hsieh et al, 2014; Kim et al, 2016; Kubo et al, 2000; Li et al, 2021; Luchetti et al, 2010; Nakajima et al, 2012; Norden et al, 2019; Popovich et al, 1997; Saber et al, 2017; Schwab et al, 2001; Takigawa et al, 2010; Wicher et al, 2017], the inflammatory disease has not been studied systematically along its entire course until recently [Kwiecien et al, 2020a]. Also, an anti-inflammatory and anti-edema tissue reaction in the spinal cord [Kwiecien 2013; Kwiecien et al, 2020a, 2021d] that appears to have a beneficial effect on the neurologic function [Kwiecien et al, 2019] and to inhibit and ultimately eliminate macrophages from the site of trauma [Kwiecien et al, 2020a] has not been previously addressed. The progressively severe astrocytic response to neurotrauma and stroke or astrogliosis is the most obvious cellular reaction associated with anti-inflammatory and anti-edema effect in the SCI [Kwiecien et al, 2020a, 2020d] and while molecular mechanisms playing role in these beneficial functions currently are unknown, their effect on the neurological scores and macrophage counts needs to be plotted in untreated animal models of neurotrauma and stroke against improvement related to experimental anti-inflammatory treatments until macrophages are eliminated from the site of injury [Kwiecien, 2021a]. This important parameter of preclinical studies on anti-inflammatory effect of experimental treatments has only recently been addressed by the author [Kwiecien et al, 2020b, Kwiecien, 2021a] but not by the others.

A cerebral vascular occlusion can cause ischemia and result in stroke. The resulting focal necrosis involving the white matter initiates severe, destructive, macrophage-rich inflammation not unlike that caused by SCI and TBI [El-dahshan et al, 2019; Jayaraj et al, 2019; Jian et al, 2019; Jin et al, 2010; Kanazawa et al, 2017; Kim et al, 2016; Lambertsen et al, 2012; Nakamura et al, 2019; Shekar et al, 2018; Zhao et al, 2017] with rodent models of stroke used to study and to treat it [Cai et al, 2019; Esposito et al, 2019; Wang et al, 2018; Zhang et al, 2019a, 2019b; Zheng et al, 2019].

While neuroinflammatory diseases discussed above are or are expected to be associated with vascular damage and cerebrospinal edema, this obvious relation has not been addressed until recently [Kwiecien et al, 2021d]. Anti-inflammatory agents therefore, are expected to inhibit vascular damage, lead to reduced fluid leakage thus limiting cerebral and spinal edema [Kwiecien et al, 2021d]. Currently, there are no satisfactorily effective treatments of inflammation at the core of pathogenesis of neurotrauma and stroke, thus effective anti-inflammatory treatments should address this shortfall.

The inhibition and elimination of the severe inflammation initiated by neurotrauma and stroke is the first and necessary step in treatment of these diseases. By inhibiting inflammation, the inflammatory damage to cerebral and spinal cord blood vessels can be reduced and eliminated and the elimination of edema fluid accelerated. Based on the understanding of the pathogenesis of neurotrauma and stroke, anti-inflammatory agents have been infused subdurally in the vicinity of the SCI lesion in the rat model and the reduction of macrophage numbers in the lesion associated with improvement of neurologic deficits was observed [Kwiecien et al, 2015, 2016, 2019, 2020b]. Although inhibitory in 1-2 weeks studies, anti-inflammatory agents did not eliminate the inflammation and it took 8 weeks of a constant subdural infusion of an effective agent to reduce numbers of phago-cytic macrophages to low levels observed in the untreated rats at 16 weeks post-SCI [Kwiecien et al, 2020a, 2020b]. The following parameters of a successful treatment to inhibit and eliminate the severe inflammation need to be considered in a neuroprotective therapy; (i) a potent anti-inflammatory agent that can reduce numbers of macrophages in the lesion; (ii) the route of administration effective in delivery of a candidate drug across or around the blood brain barrier (BBB) to the lesion. While the intralesional administration has proven effective via subdural infusion and also by delivery of an anti-inflammatory agent from an implanted hydrogel [Kwiecien et al, 2019, 2020b, 2020c] it involves invasive neurosurgery. A systemic administration, such as oral or intravenous, while much less invasive and more practical to administer, needs to take under consideration the effect of inflammatory damage to the BBB- and to the brain spinal cord barrier (BSCB) and a damage-counteracting effect of astroglial reaction directed at restoring the BBB and/or BSCB. (iii) The duration of sustained administration of an anti-inflammatory agent has to be sufficient to eliminate macrophages from the lesion [Kwiecien et al, 2020b, 2021a]. A successful anti-inflammatory treatment in neurotrauma and stroke will reduce the damage to the CNS around the initial traumatic, ischemic lesion and will accelerate elimination of edema leading to reduction in neurologic deficits and improved quality of life in acute patients, particularly those where the traumatic or ischemic injury is not extensive. In patients with large traumatic or stroke lesions, an effective anti-inflammatory treatment may not restore enough neurological function by itself for acceptable quality of life, but it will allow for the application of tissue engineering therapies leading to neuroregeneration and greater degree of restoration of neurologic function [Kwiecien, 2021b; Kwiecien, 2022]. Such neuroengineering therapies are not considered possible when the severe destructive inflammation is active. Novel methods to measure the anti-inflammatory activity of a candidate agent have been developed in the rat model of SCI.

In the Hind End Locomotor test, performed once every day in unrestrained rats in the cage, the motor function is measured with movements of both hind legs scored 0-6 with 0=complete paralysis and 6=normal gait [Kwiecien et al, 2019, 2020b, 2020c].

In the Toe Pinch Withdrawal test, performed once every day in rats held by the tail, the sensory function and the strength of both hind limbs are scored 0-6 with 0=complete loss of reaction to the toe pinch and 6=strong, normal withdrawal in both legs after the toe pinch [Kwiecien et al, 2019, 2020b, 2020c].

The Body Weight Change after the SCI surgery is recorded every $3^{rd}$ day [Kwiecien et al, 2019, 2020b 2021c].

The histologic examination is performed in the series of consecutive sections, 3 mm thick, of the spinal cord including the lesion, stained with luxol fast blue and counterstained with hematoxylin and eosin (LFB+H&E). A necrotic and hemorrhagic lesion deep in the spinal cord is infiltrated starting at the day 3, by numerous inflammatory, CD68+/CD163− macrophages that phagocytize myelin-rich necrotic debris and red blood cells. The numbers of macrophages rapidly increase and remain high for 4 weeks after SCI after which they gradually decline [Kwiecien et al, 2020a]. Within the first week post-SCI the deep lesion is transformed into a cavity of injury (COI) when it starts to accumulate excess water from edema in the surrounding spinal cord [Kwiecien et al, 2020a, 2021d]. The macrophage count is performed in a COI in the injured spinal cord of untreated and treated rats in a standardized fashion at fixed periods of time post-surgery to determine a degree of reduction of macrophage numbers related to a tested anti-inflammatory agent [Kwiecien et al, 2019; 2020a, 2020b, 2021c]. This reduction in numbers of macrophages plotted against such numbers in controls is reliably indicative of a therapeutic effect of an anti-inflammatory agent.

Xanthohumol (2',4',4-trihydroxy-6'-methoxy-3'-prenyl-chalcone) is a major chalcone derived from hops (*Humulus lupulus* L.) [Lee et al, 2011] isolated by stages of elution by organic solvents [Stevens & Page, 2004]. Total synthesis of xanthohumol has been described [Khupse & Erharddt, 2007]. In in vitro and in pre-clinical studies on mechanistic and therapeutic activities of xanthohumol indicate a vast array of beneficial activities in inflammatory, neoplastic, infectious and metabolic diseases [Doddapattar et al, 2013; Lima-Fontes et al, 2017; Miranda et al, 2016; Monteiro et al, 2008; Negrao et al, 2010, Nozawa et al, 2005; Yamaguchi et al, 2008]. The interest in xanthohumol as a therapeutic agent has led to a clinical trial phase 1 in healthy volunteers, approved by the Food and Drug Administration, USA, designed to test it for potential toxicity [Bradley et al, 2020]. Powerful anti-inflammatory activity of xanthohumol has been shown in animal models of hepatitis [Dorn et al, 2010a, 2013; Yang et al, 2013], pneumonia [Lv et al, 2017], cisplatin induced nephrotoxicity [Li et al, 2018], allergic dermatitis [Cho et al, 2010], skin wound healing in type 1 diabetes mellitus mice [Costa et al, 2013] and in normal rats [Negrao et al, 2010, 2012], osteoarthritis [Chen et al, 2021; Khayyal et al, 2020; Zhang et al, 2021], colitis [Cho et al, 2017], atherosclerotic plaque formation [Doddapattar et al, 2013], and attributed to inhibition of nuclear factor NF-κB [Chen et al, 2008; Cho et al, 2008; Dorn et al, 2010a], pro-inflammatory cytokines including IL-1β, TNF-α, IL-6, Il-12 [Cho et al, 2008, 2010] and other pro-inflammatory factors including iNOS [Cho et al, 2008]. In vitro studies have shown potent inhibition of pro-inflammatory macrophage activity by xanthohumol including reduction of IL-1β, TNF-α and macrophage chemoattractant protein-1 [Chen et al, 2008; Lupinnaci et al, 2009]. Anti-inflammatory and anti-oxidative activities of xanthohumol in mouse BV2 microglia were shown to be related to elevation of NRF2 protein and inhibition of nuclear factor NF-κB, IL-1β and TNF-α [Lee et al, 2011]. Xanthohumol has been shown to have neuroprotective activity in a mouse model of retinal degeneration [Henneman et al, 2018], in age-related inflammatory and apoptotic brain damage in male senescence-accelerated prone mice [Rancan et al, 2017], in ischemic rat model [Yen et al, 2012], in kainic acid excitotoxicity in rats [Wang et al, 2020] and also in an in vitro study where it also had a neuroprotective effect and promoted neuronogenesis and axonal growth [Oberbauer et al, 2013] suggesting the systemic administration of xanthohumol as potentially useful adjunctive agent in neuroregenerative therapies. In a rat model of stroke, xanthohumol, has been shown to limit the size of the lesion [Jiao et al, 2020; Yen et al, 2012], however, its anti-inflammatory activity in this model has not been demonstrated. The oral administration of xanthohumol has been shown to result in low bioavailability likely related to metabolic degradation by intestinal microflora [Legette et al, 2012, Nookandeh et al, 2004, Stevens & Page, 2004]. Since xanthohumol dissolves in the water poorly, addition of ethyl alcohol, cremophor, tween20, propylene glycol, its micellar solubilization or Hydroxypropyl-β-cyclodextrin complexing, to increase its solubility for topical, oral or parenteral administration have been attempted with considerable success [Henneman et al, 2018; Husson et al, 2005; Khayyal et al, 2020; Kirchinger et al, 2019; Legette et al, 2012].

While the oral administration of XN results in poor bioavailability, approximately 1%, the amount of XN in blood plasma appears to be elevated with increasing oral dosing in mice, rats and humans [Legette et al., 2012; Neumann et al., 2022]. There is a direct therapeutic consequence of this since increasing oral doses of XN resulted in increasingly better scores of neurological deficits with their faster recovery coinciding with remarkable inhibition of macrophage counts in the cavity of injury (COI) combined with accelerated elimination of macrophages from the COI [Kwiecien, 2022]. The most comprehensive study on pharmacology of hops XN in Wistar rats [Nowak et al, 2020] indicates that oral administration of 40 to 200 mg/kg results in declining bioavailability corresponding to 1.16 to 0.53% respectively. The half-life of 10 mg/kg XN administered intravenously is 7.67 hours while it is 21 to 23 hours after oral administration of 40 to 200 mg/kg [Nowak et al, 2022]. Relatively short duration of xanthohumol bioavailability in blood indicates a need for multiple oral administrations per day or the continuous parenteral administration to maintain its optimal therapeutic level. Specific studies on rats and mice revealed no toxicity after long administration of large doses of xanthohumol [Dorn et al, 2010b; Husson et al, 2005; Vanhoecke et al, 2005].

BRIEF SUMMARY OF THE INVENTION

A method to treat the spinal cord injury (SCI), traumatic brain injury (TBI), neurosurgical resection, stroke and cerebral edema and spinal cord edema by the oral administration of 5 mg xanthohumol or similar per day for a period of 8 weeks or similar is described in the rat model of SCI. This treatment approximates 15 mg/kg body weight and has the anti-inflammatory effect and causes neuroprotection in the SCI rats with improvement of neurologic functions and other clinical signs. The neurologic function was measured by novel methodology designed to broaden examination of a variety of functions improving after the SCI and to increase its robustness; the Hind End Locomotor Function test, the Toe Pinch Withdrawal test and the Duration of Paralysis of the Urinary Bladder. The body weight measurements were taken as well. While phagocytic macrophages are the main cellular effector in a severe, destructive and long-lasting inflammation, the Macrophage Count in the Cavity of Injury (COI) was performed. The administration of xanthohumol was performed twice a day and this frequency and the dosing itself can be increased since toxicity of xanthohumol was not observed. The improvements in neurologic deficits and in accelerated reduction and elimination of phagocytic macrophages on histologic examination indicate a reduced inflammatory damage to the spinal cord surrounding the lesion and also, indicate an accelerated reduction and elimination of spinal cord edema therein. The treatment with xanthohumol presented here is novel, effective and the first and necessary anti-inflammatory treatment in neurotrauma including the SCI, TBI, and the neurosurgical resection and in stroke.

BRIEF DESCRIPTION OF THE DRAWINGS

FIG. 4. Shows the Body Weight Change in rats every $3^{rd}$ day and expressed as average of percentage of the body weight taken before the surgery. The Analysis of Variance (ANOVA) was performed to obtain p-values. While rats treated with xanthohumol for 4 and for 6 weeks recovered the body weight faster and better than untreated controls, there was no statistical difference between both groups of rats in 1, 2 and 8 weeks post-SCI.

DETAILED DESCRIPTION OF THE INVENTION

Figure 1:
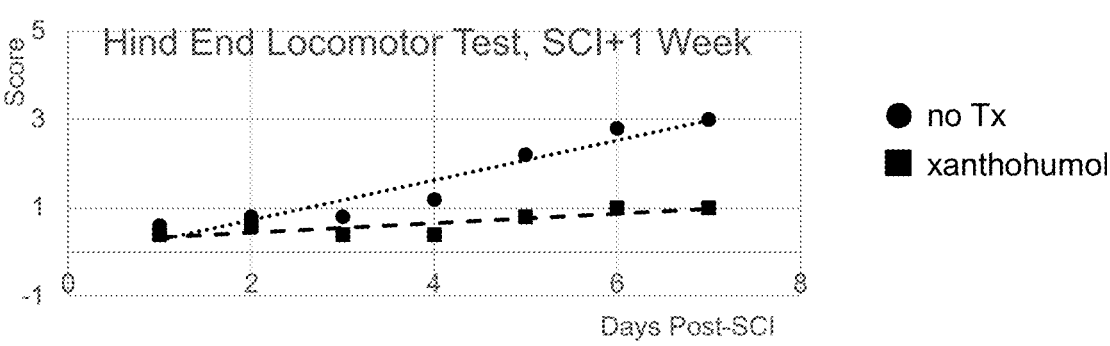
FIG. 1. Shows the results of the Hind End Locomotor test was performed on rats in groups treated with xanthohumol, surviving for 1-8 weeks post-SCI. Analysis of Variance (ANOVA) was performed to obtain an overall F-value for the model as well as individual T-values. At the same time p-values were produced for the overall model and individual variables. This was done for 1 week, 2 week, 4 week, 6 week, and 8 week study groups. The effect of the treatment was statistically significant for each group with duration 2-8 weeks post-SCI.
Figure 1:
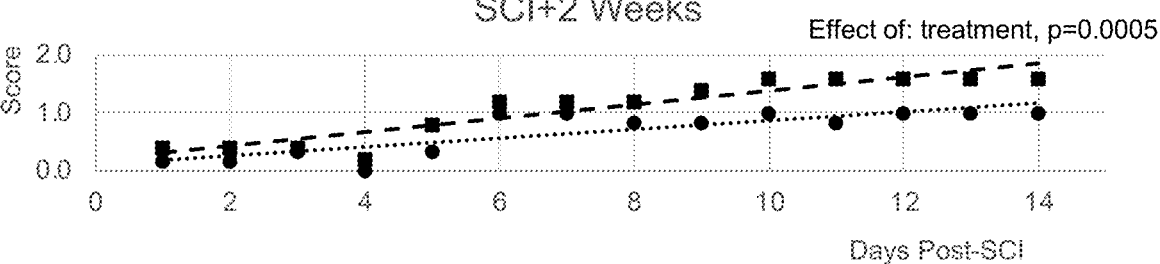
Figure 1:
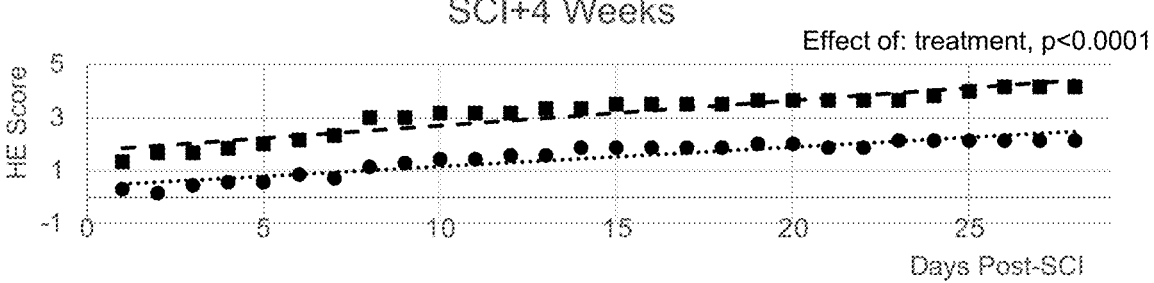
Figure 1:
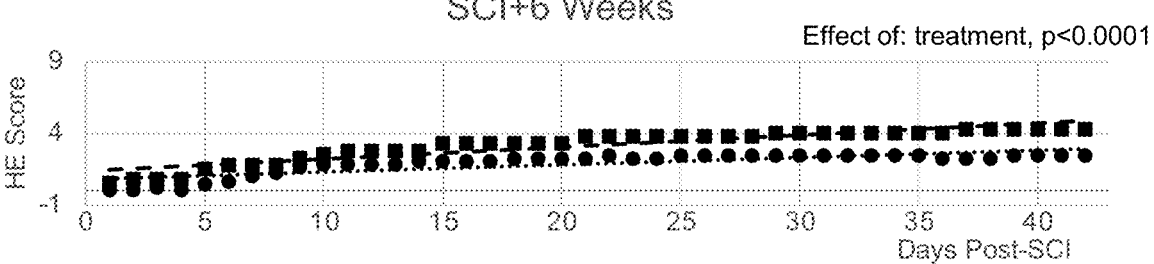
Figure 1:
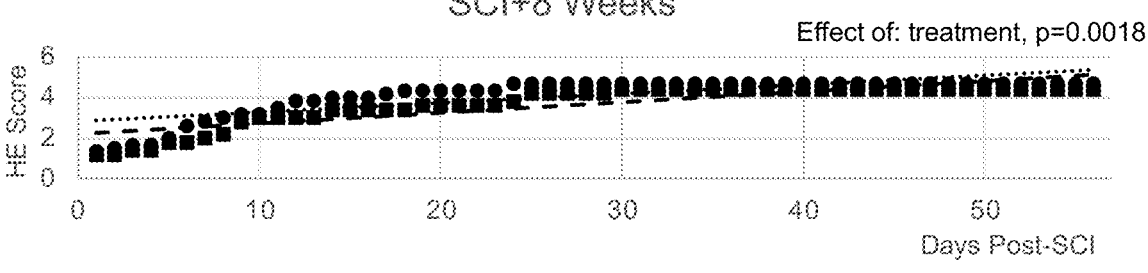
Figure 2:
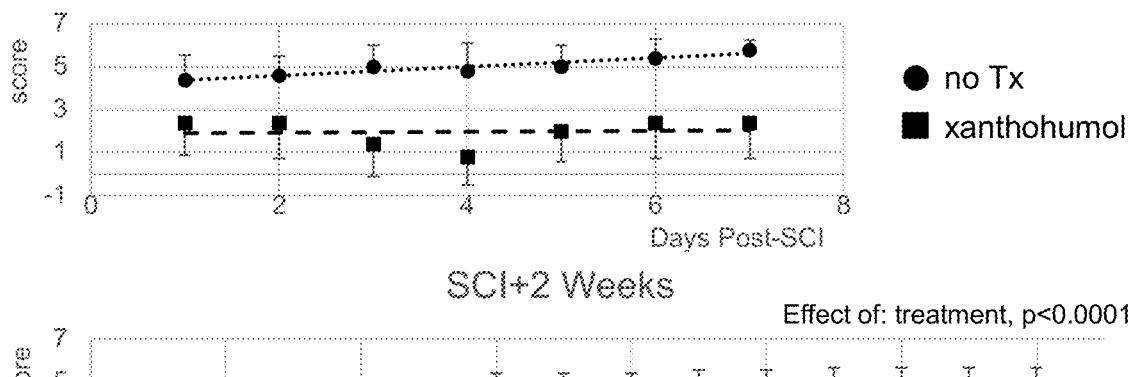
FIG. 2. Shows the results of the Toe Pinch Withdrawal test in rats treated with xanthohumol, for 1-8 weeks post-SCI. The analysis of variance (ANOVA) was performed, p-values were produced for the overall model and individual variables. The effect of the treatment was statistically significant for groups with duration 2-8 weeks post-SCI.
Figure 2:
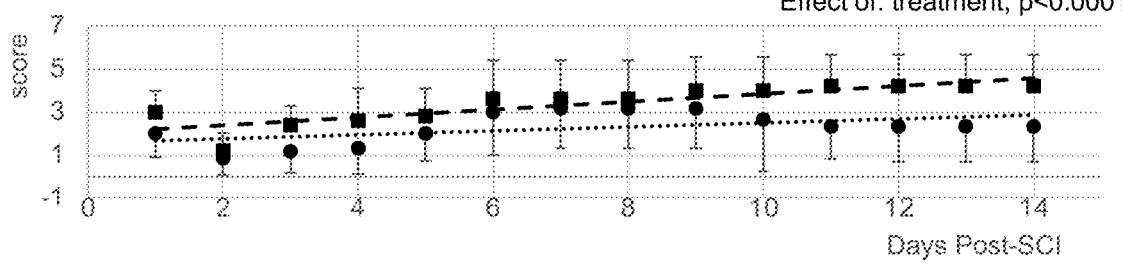
Figure 2:
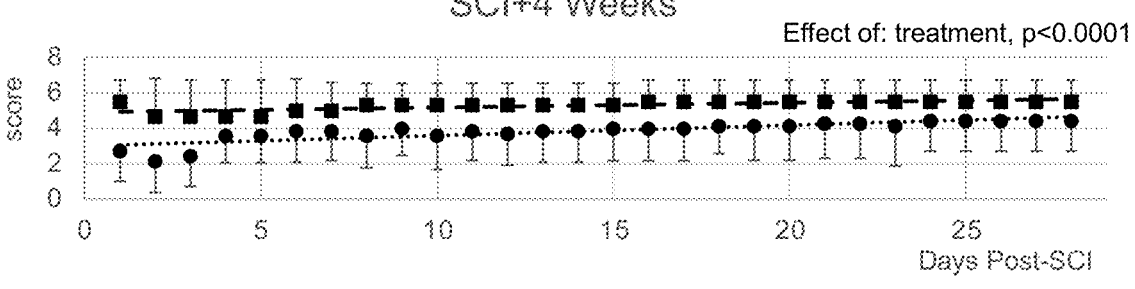
Figure 2:
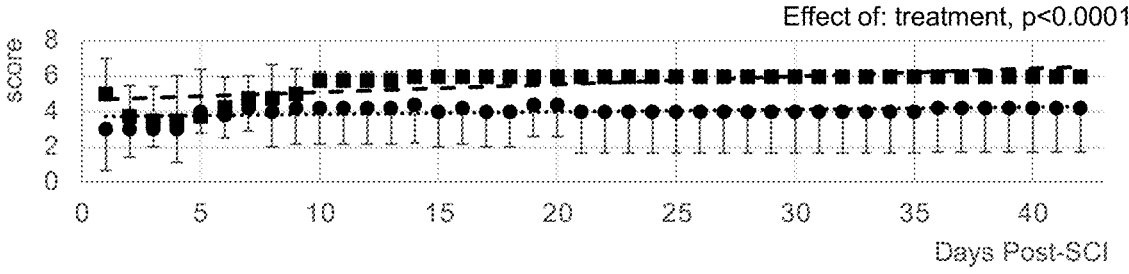
Figure 2:
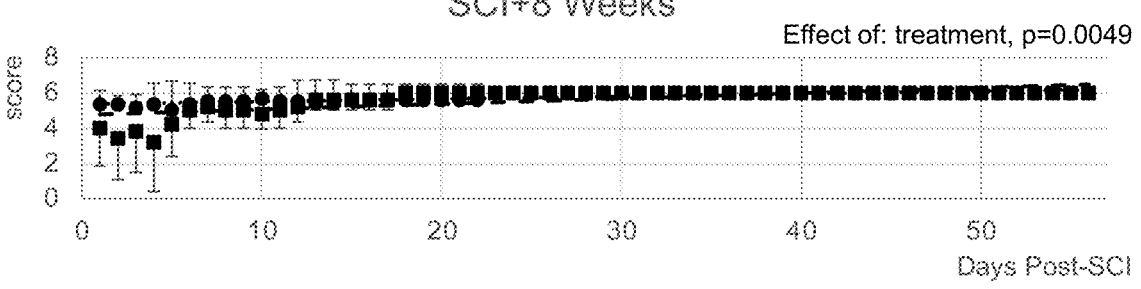

The spinal cord injury model in the rat.

Healthy male Long Evans rats aged 12 weeks, 330-360 g, were offered a fruit flavored jello cube twice a day for 1 week prior to the surgery and were separated in individual cages 3 days before the surgery. Rats were induced with 5% isoflurane in 95% oxygen flowing at a rate of 1 liter per minute and maintained at 3.5% isoflurane in 96.5% oxygen. The anaesthetized rats had the skin on the back shaved and prepared for surgery with 70% ethyl alcohol and 10% iodine swabs. The skin was cut over the caudal thoracic and lumbar spine and spinal muscles dissected from the vertebral spine of the thoracic 10 (T10) vertebrum and the dorsal arches of this vertebrum removed. A 3Fogarty catheter was inserted via this laminectomy over the intact dura towards the head to place the caudal edge of the 3 mm long balloon at 1 cm rostral to the laminectomy. The balloon was inflated with 15 UL of sterile saline for 3 minutes, then deflated and the catheter removed. The spinal muscles were closed with absorbable sutures over the laminectomy and the skin incision was closed with stainless steel staples. Before awakening, the rats were administered; 50 µL of a painkiller Anafen (ketoprofen, 100 mg/mL, Merial) subcutaneously for pain, and 50 UL of Baytril antibiotic (enrofloxacin 50 mg/mL, Bayer) intramuscular, and 3 mL of saline subcutaneous. In the initial experiment designed to determine the anti-inflammatory effect of 0.2, 1.0 and 5 mg per day of xanthohumol (Sigma-Aldrich) after the surgery, the rats were offered a jello cube with half of the above dose twice a day, at 8-9 hours and 15-16 hours intervals, and the consumption of the jello cube was observed and recorded every day for 7 days. Each treatment group had 5 rats. In the second phase of the experiment 1 jello cube alone or jello cube with 2.5 mg xanthohumol was offered twice a day for 1, 2, 4, 6, and 8 weeks. Each treatment group had 6-7 rats.

Given the invasive nature of the SCI model, an ethical Endpoint was instituted. A rat with distended urinary bladder that was impossible to express or was ruptured, or with severe dehydration and with hypothermia and lethargy was humanely euthanized and not used in the study. The rats were administered Anafen painkiller once daily for 2 days post-surgery and rats with distended urinary bladder were given Baytril antibiotic once daily for 5 days post-surgery. Rats with moderate dehydration were administered with 5-10 mL saline subcutaneously once or twice a day as needed. Rats with distended urinary bladder and micturition resulting in soiling of the perineal area had the bladder gently manually expressed twice a day and had a bath of the hind end in warm clean water done every 2 days until the bladder function returned.

The clinical tests:

1. The Hind End Locomotor test [Kwiecien et al, 2021c] was performed in freely moving rats in the cage once a day. The motor function of the hind limbs was scored from 0-6 where 0=complete paralysis of both hind legs and 6=normal locomotion.

2. The Toe Pinch Withdrawal test [Kwiecien et al, 2021c] was performed once a day in rats held by the tail in the cage and the presence and strength of both hind legs scored 0-6 where 0=no response to the toe pinch and 6=strong, normal withdrawal response to the toe pinch in both legs.

3. The balloon crush SCI and spinal bone and muscle trauma related to the surgery resulted in a body weight loss that was transient and recovered over a period of a few weeks. The rats were weighed every $3^{rd}$ day.

4. The duration of the distention of the urinary bladder that required manual voiding until the normal function of the urinary bladder was restored, in days, was recorded.

At a required experimental time point; 1, 2, 4, 6, or 8 weeks post-surgery, the SCI rats were overdosed with the sodium pentobarbital (80 mg/kg b.w.) administered intraperitoneally. When in deep plane of anaesthesia, the chest was cut open, 100 international units of heparin sodium injected into the left heart ventricle and a cannula with flowing lactated Ringer's solution inserted into the left ventricle while the right auricle was cut open. After the blood was washed out, the flow of the lactated Ringer's solution was replaced by that of phosphate buffered formalin and the carcass was fixed.

The spine was removed, postfixed in formalin overnight and then placed in formalin supplemented with 8% EDTA, pH 7.0, to decalcify the spinal vertebrae. The decalcifying solution was replaced by fresh one every 2 days for 2 weeks. Once soft, the spine was cut perpendicular to its long axis into 3 mm thick segments starting from laminectomy rostrally to include the SCI lesion. Eight segments were processed in rising concentrations of ethyl alcohol and xylene, embedded in paraffin wax, cut 5 μm thick and mounted on the glass slide. The sections were stained with luxol fast blue and counterstained with hematoxylin and eosin (LFB+H&E) and coverslipped. Stained sections were examined by the experienced experimental neuropathologist (the author) under a Nikon Eclipse 50i light microscope and the spinal cord photographed. At 40× magnification a margin of one COI per section, including 20% of the spinal cord and 80% of the COI was digitally photographed. The 40× magnification images were then analyzed and macrophages; large cells with a round, oval, sometimes subcleaved nucleus with abundant cytoplasm containing blue granules of myelin debris and/or red blood cells [Kwiecien et al, 2015, 2016, 2019, 2020a, 2020b, 2021c], were counted. The counts were averaged for a rat and these averages averaged for a treatment group.

Results of this study on the anti-inflammatory effect of xanthohumol administered orally to rats with the SCI are demonstrated in FIGS. 1-7.

Details of statistical analysis of clinical data and of macrophage count data are provided respectively in the Brief Description of Drawings for FIGS. 1-6.

The Hind End Locomotor test (FIG. 1) revealed significantly higher scores for xanthohumol-treated rats vs untreated rats in treatment groups 2-8 weeks post-SCI, indicating beneficial effect of the treatment on a faster and stronger recovery of the motor function in the hind legs of SCI rats.

In the Toe Pinch Withdrawal test (FIG. 2), xanthohumol-treated SCI rats performed statistically better than untreated rats in treatment groups 2-8 weeks post-SCI, indicating beneficial effect of the treatment on the return of pain sensation and of withdrawal strength in the hind limbs.

Figure 3:
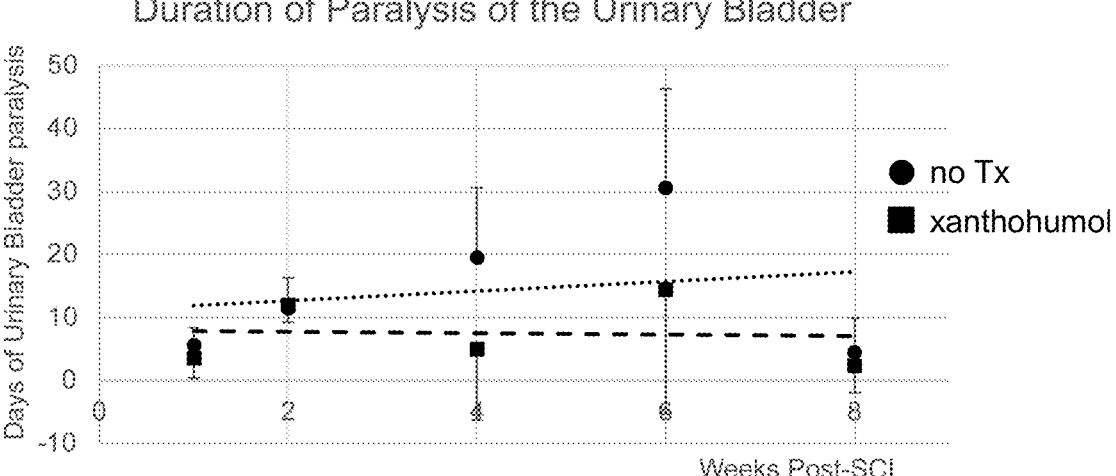
FIG. 3. Shows the Duration of Paralysis of the Urinary Bladder performed in rats treated with xanthohumol for 1-8 weeks post-SCI. The Analysis of Variance (ANOVA) was performed and p-values were produced. The effect of the treatment was statistically significant for the 4 weeks post-SCI group but not for other groups although there was the tendency for xanthohumol rats to recover bladder function faster in the 6 weeks post-SCI group.

The duration of the distention of the urinary bladder due to its paralysis, that required manual voiding until the normal function of the urinary bladder was restored, is shown in FIG. 3. In the rats treated with xanthohumol recovery of the bladder function occurred significantly faster than in untreated rats in 4 weeks treatment group but not in other treatment groups, although in the 6 weeks treatment group there was a tendency for the paralyzed urinary bladder to recover faster than in controls. This novel previously not used test may indicate that the faster recovery of the urinary bladder function may be related to anti-inflammatory effect of xanthohumol and to related reduction to vascular damage and leaking of edema fluid in the spinal cord around and caudal to the lesion. Similar anti-inflammatory and edema-inhibiting mechanism may be of therapeutic benefit to the recovery of the breathing function, of the bowel function and to sexual performance.

The body weight loss post-surgery and its recovery are presented in FIG. 4. While the body weight loss occurred in un-treated and in xanthohumol-treated SCI rats for the first 2 weeks, it recovered statistically sooner and to a greater degree in xanthohumol-treated rats than in untreated controls in groups treated for 4 and 6 weeks. This observation indicates that negative effects of the post-SCI inflammation included lower food intake in un-treated rats than in xanthohumol-treated rats.

Figure 5:
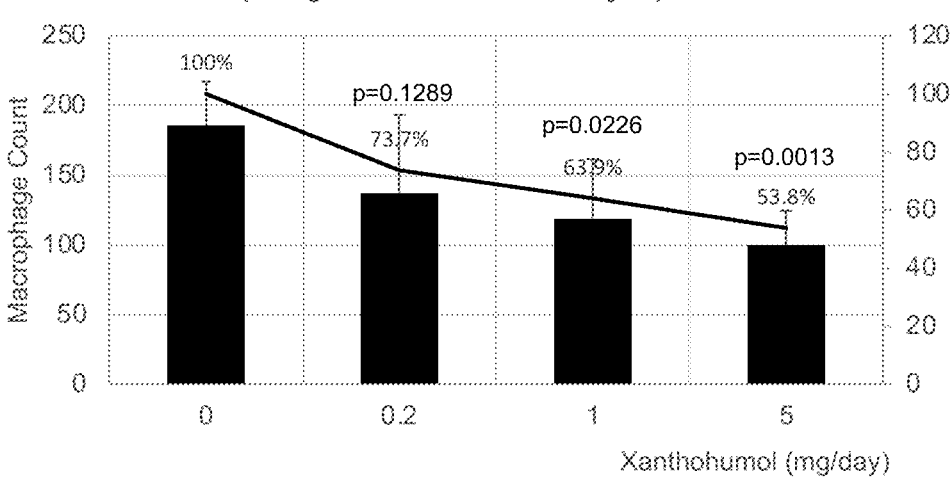
FIG. 5. Shows the dose-response to treatment with xanthohumol analysed in the Macrophage Counts in the Cavity of Injury (COI) in SCI rats. All 3 treatment doses of xanthohumol had a macrophage-lowering effect with a clear dose-response effect which was statistically significant for 1.0 and 5.0 mg/rat/day but not for 0.2 mg/rat/day.

The dose of xanthohumol of 5 mg per day was selected after performing a 7 days study on the SCI rats offered jello cubes with 0, 0.2, 1.0 and 5.0 mg of this agent. The Macrophage Count in the COI test revealed that there was a dose response reduction in macrophage numbers at 73.7, 63.9, and 53.8% of the untreated controls (100%) (FIG. 5). The dosage of xanthohumol was calculated per kg body weight of average weight of treated rats before the surgery and it was 0.6, 3.0 and 14.5 g respectively (see Table in FIG. 5). The macrophage-reducing effect was caused by all 3 doses of xanthohumol, but this effect was dose-dependent and significant for 1.0 mg/rat/day (p=0.026) and for 5.0 mg/rat/day (p=0.0013). A 16.9 mg/kg body weight dose of daily oral administration of xanthohumol in rats revealed no toxic effect [Leggete et al, 2012] therefore, 5 mg of xanthohumol was offered in two 2.5 mg daily doses in the fruit jello to SCI rats in post-SCI studies conducted for 1, 2, 4, 6, and 8 weeks. This dose averaged 14.5 mg/kg body weight in rats immediately before SCI (see FIG. 5) and became higher than 14.5 mg/kg in rats post-SCI due to the body weight-lowering effect of this surgery (see FIG. 4).

Figure 6:
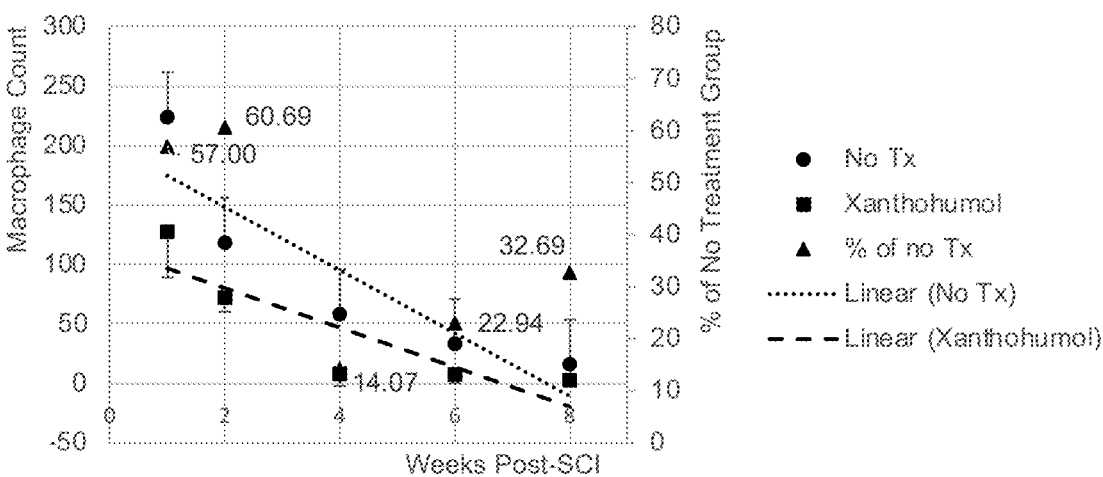
FIG. 6. Shows the reducing effect of 5 mg/rat/day of xanthohumol on macrophage counts and anti-inflammatory effect in the rat model of SCI. The macrophage counts in the COI, were gradually reduced from a highest at 1 week to the lowest at 8 weeks post-SCI in untreated rats and more so in xanthohumol-treated rats. The triangle-shaped black markers indicate average % macrophage counts of xanthohumol treated rats vs untreated controls and these percentages are indicated at each time point from 1-8 weeks post-SCI. While the averages of the macrophage counts were lower in xanthohumol-treated rats at each time point post-SCI, they were statistically different for groups 1-6 weeks post-SCI but not for the group analysed at 8 weeks. The Analysis of Variance (ANOVA) was performed to obtain p-values. This was done for 1 week, 2 week, 4 week, 6 week, and 8 week study groups. Another ANOVA was performed incorporating time in days as a second independent variable.
Figure 7:
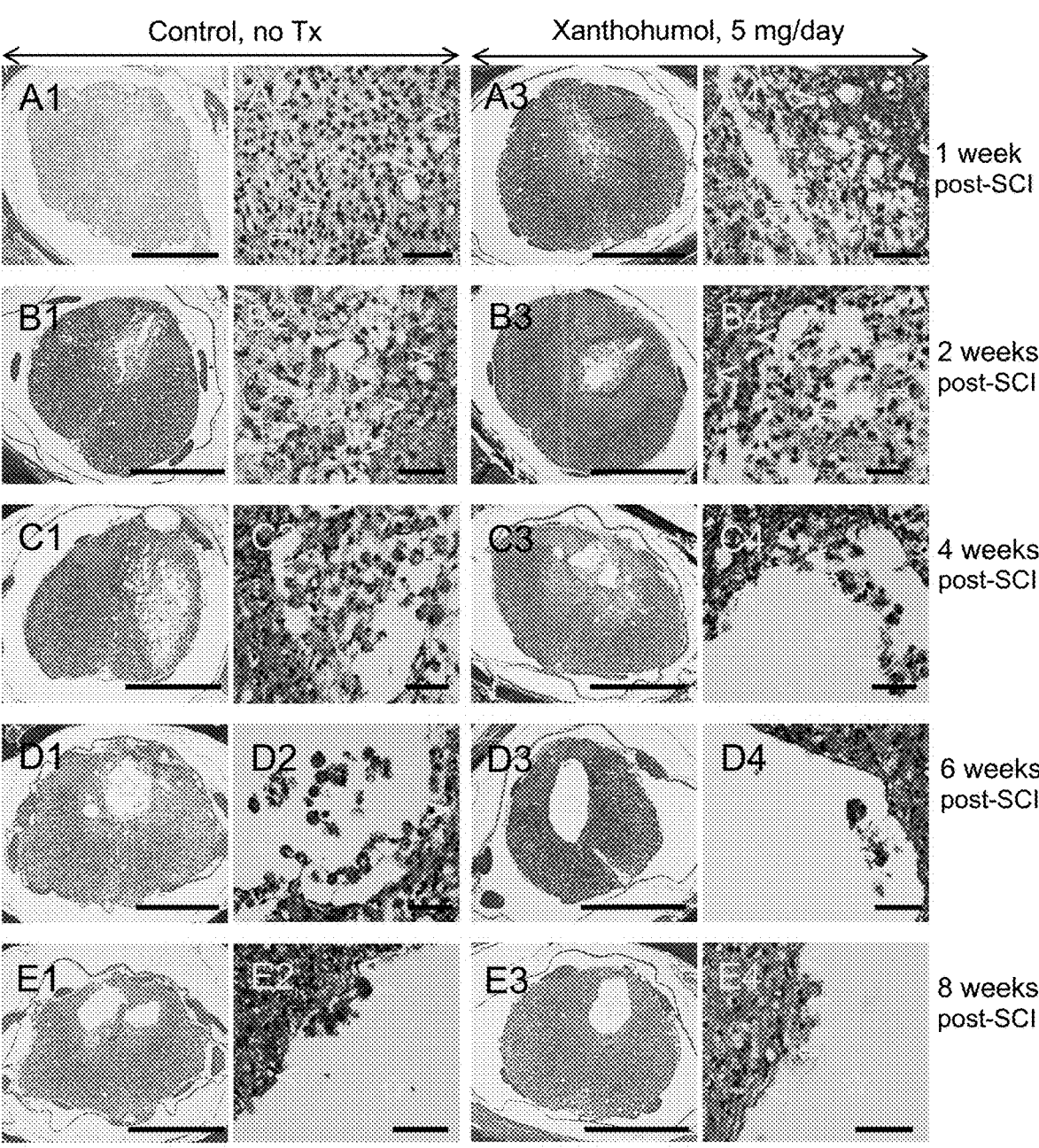
FIG. 7. Shows color microphotographs with histologic representation of the SCI in the rat model at 1-8 weeks post-SCI. The sections of the spinal cord contain a traumatic lesion converted into a cavity of injury (COI) indicated by a yellow star and delineated by the surrounding spinal cord (yellow arrowheads). The COI is infiltrated by macrophages (indicated by an open yellow arrow); large cells with a round or oval nucleus and large cytoplasm containing blue granules of myelin and/or red blood cells. The greatest numbers of macrophages are at 1 week post-SCI and then gradually decline at weeks 2-8 in untreated rats (column 2). In xanthohumol-treated rats numbers of macrophages in the COI are reduced at each time point post-SCI (column 4) and are rare or absent at 6 and 8 weeks post-SCI. Size bars; 1 mm for micrographs in columns 1 and 3; 50 µm for micrographs in columns 2 and 4. Luxol fast blue counterstained with hematoxylin and eosin (LFB+H&E).

The results of the macrophage counts in un-treated rats and in rats treated with 5 mg xanthohumol per day are presented in the FIG. 6. While the numbers of macrophages in the COI in un-treated rats gradually declined after the 1st week due to an anti-inflammatory response by the spinal cord [Kwiecien et al, 2020a], the treatment with xanthohumol consistently accelerated reduction of these numbers at each study time point with statistical difference for 1-6 weeks treatment groups and not for 8 weeks treatment group. The macrophage counts in xanthohumol treated rats were lower at; 57.0, 60.7, 14.1, 22.9, and 32.7% of the controls respective to 1, 2, 4, 6, and 8 weeks post-SCI. These results indicate a powerful anti-inflammatory effect of orally administered xanthohumol resulting in reduction and accelerated elimination of phagocytic macrophages from the lesion initiated by the spinal cord injury. Since CD68+/CD163-pro-inflammatory macrophages persist in the COI and continue to destroy myelin in untreated rats beyond 16 weeks post-SCI [Kwiecien et al, 2020a], the anti-inflammatory effect of xanthohumol treatment evidenced as lowering numbers of phagocytic macrophages and accelerating their elimination, can be interpreted as neuroprotective in the SCI and also in the TBI and in stroke. The morphologic results of histologic analysis of the COI un-treated and xanthohumol-treated rats at 1, 2, 4, 6, and 8 weeks post-SCI are presented in the FIG. 7.

The invention claimed is:

1. A method of reducing the number of macrophage cells at a cavity of injury in a central nervous system in an animal, the method comprising oral administration to the animal of a treatment dose of 1-5 mg per 330-360 grams body weight per day of xanthohumol.

2. The method of claim 1, which inhibits neuroinflammation.

3. The method of claim 2, wherein the neuroinflammation is in the brain.

4. The method of claim 2, wherein the neuroinflammation is in spinal cord.

5. The method of claim 2, wherein the animal has spinal cord injury (SCI).

6. The method of claim 2, wherein the animal has traumatic brain injury (TBI).

7. The method of claim 2, wherein the animal has had a stroke.

8. The method of claim 1, which additionally inhibits edema.

9. The method of claim 5, wherein the animal exhibits improved locomotor function as compared to an untreated control.

10. The method of claim 5, wherein the animal exhibits a reduction in time of paralysis as compared to an untreated control.

11. The method of claim 1, wherein the animal has Alzheimer's disease.

12. The method of claim 1, wherein the animal has frontotemporal dementia.

13. The method of claim 1, wherein the animal has Parkinson's disease.

14. The method of claim 1, wherein the animal has Amyotrophic Lateral Sclerosis.

15. The method of claim 1, wherein the animal has multiple sclerosis.

16. The method of claim 1, wherein the animal has neuromyelitis optica.

17. The method of claim 1, wherein the animal has immune mediated myeloencephalitides.

18. The method of claim 1, wherein the animal is a human.

19. The method of claim 1, wherein the daily treatment dose of xanthohumol is about 3 to 14.5 mg/kg body weight.

20. The method of claim 1, wherein the xanthohumol reduced macrophage number at the cavity of injury by at least about 20-40% in a week.

* * * * *